(12) United States Patent
Martin

(10) Patent No.: US 9,398,905 B2
(45) Date of Patent: Jul. 26, 2016

(54) CIRCULAR NEEDLE APPLIER WITH OFFSET NEEDLE AND CARRIER TRACKS

(71) Applicant: Ethicon Endo-Surgery, Inc., Cincinnati, OH (US)

(72) Inventor: David T. Martin, Milford, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 316 days.

(21) Appl. No.: 13/832,786

(22) Filed: Mar. 15, 2013

(65) Prior Publication Data

US 2014/0171972 A1    Jun. 19, 2014

Related U.S. Application Data

(60) Provisional application No. 61/736,678, filed on Dec. 13, 2012, provisional application No. 61/736,682, filed on Dec. 13, 2012, provisional application No. 61/736,690, filed on Dec. 13, 2012, provisional application No. 61/736,696, filed on Dec. 13, 2012.

(51) Int. Cl.
*A61B 17/04* (2006.01)
*A61B 17/06* (2006.01)
(Continued)

(52) U.S. Cl.
CPC ......... *A61B 17/0469* (2013.01); *A61B 17/0482* (2013.01); *A61B 17/0483* (2013.01); *A61B 17/0491* (2013.01); *A61B 17/0625* (2013.01); *A61B 17/06114* (2013.01);
(Continued)

(58) Field of Classification Search
CPC ........... A61B 17/0483; A61B 17/0469; A61B 17/04; A61B 17/06114; A61B 17/0625; A61B 17/0482; A61B 17/062; A61B 2017/2927; A61B 2017/0608; A61B 2017/2929; A61B 5/14; A61B 5/15; A61B 5/150282; A61B 5/150427; A61B 5/15115; A61M 5/32
USPC ........................... 606/144, 147, 181; 600/583
See application file for complete search history.

(56) References Cited

U.S. PATENT DOCUMENTS 1,579,379 A    4/1926    Marbel
1,822,330 A    9/1931    Ainslie
(Continued)

FOREIGN PATENT DOCUMENTS

DE    4310315        10/1993
EP    0674875 A1    10/1995
(Continued)

OTHER PUBLICATIONS

U.S. Appl. No. 13/792,947, filed Mar. 11, 2013 by Ethicon Endo-Surgery, Inc.
(Continued)

*Primary Examiner* — Eric Rosen
*Assistant Examiner* — George J Ulsh

(57) ABSTRACT

A surgical suturing device comprises an arced needle track. An arced needle is positioned in the needle track, the needle having a leading end, a trailing end, a medial face, and a lateral face. A length of suture is connected to the needle. An arced carrier track is spaced from the needle track. A reciprocating needle driver has a carrier positioned in the carrier track and a driver positioned in the needle track and is operative to engage and move the needle in the needle track. A transmission is operative to reciprocate the carrier in the carrier track.

17 Claims, 30 Drawing Sheets

(51) Int. Cl.
*A61B 17/062* (2006.01)
*A61B 17/00* (2006.01)
*A61B 17/29* (2006.01)
*A61B 17/072* (2006.01)

(52) U.S. Cl.
CPC .. *A61B 17/06123* (2013.01); *A61B 2017/0023* (2013.01); *A61B 2017/00473* (2013.01); *A61B 2017/0608* (2013.01); *A61B 2017/07271* (2013.01); *A61B 2017/2927* (2013.01)

(56) References Cited

U.S. PATENT DOCUMENTS

| | | |
|---|---|---|
| 1,884,149 A | 10/1932 | Nullmeyer |
| 2,291,181 A | 7/1942 | Alderman |
| 3,168,097 A | 2/1965 | Dormia |
| 3,598,281 A | 8/1971 | Watermeier |
| 3,749,238 A | 7/1973 | Taylor |
| 4,027,608 A | 6/1977 | Arbuckle |
| 4,123,982 A | 11/1978 | Bess, Jr. et al. |
| 4,196,836 A | 4/1980 | Becht |
| 4,235,177 A | 11/1980 | Arbuckle |
| 4,406,237 A | 9/1983 | Eguchi et al. |
| 4,417,532 A | 11/1983 | Yasukata |
| 4,440,171 A | 4/1984 | Nomoto et al. |
| 4,557,265 A | 12/1985 | Andersson |
| 4,899,746 A | 2/1990 | Brunk |
| 5,209,747 A | 5/1993 | Knoepfler |
| 5,282,806 A | 2/1994 | Haber et al. |
| 5,289,963 A | 3/1994 | McGarry et al. |
| 5,306,281 A | 4/1994 | Beurrier |
| 5,308,353 A | 5/1994 | Beurrier |
| 5,318,578 A | 6/1994 | Hasson |
| 5,383,888 A | 1/1995 | Zvenyatsky et al. |
| 5,389,103 A | 2/1995 | Melzer et al. |
| 5,403,347 A | 4/1995 | Roby et al. |
| 5,403,354 A | 4/1995 | Adams et al. |
| 5,437,681 A | 8/1995 | Meade et al. |
| 5,454,823 A | 10/1995 | Richardson et al. |
| 5,470,338 A | 11/1995 | Whitfield et al. |
| 5,478,344 A | 12/1995 | Stone et al. |
| 5,478,345 A | 12/1995 | Stone et al. |
| 5,480,406 A | 1/1996 | Nolan et al. |
| 5,527,321 A | 6/1996 | Hinchliffe |
| 5,540,704 A | 7/1996 | Gordon et al. |
| 5,540,705 A | 7/1996 | Meade et al. |
| 5,540,706 A | 7/1996 | Aust et al. |
| 5,553,477 A | 9/1996 | Eisensmith et al. |
| 5,554,170 A | 9/1996 | Roby et al. |
| 5,560,532 A | 10/1996 | DeFonzo et al. |
| 5,569,301 A | 10/1996 | Granger et al. |
| 5,571,090 A | 11/1996 | Sherts |
| 5,591,181 A | 1/1997 | Stone et al. |
| 5,593,421 A | 1/1997 | Bauer |
| 5,610,653 A | 3/1997 | Abecassis |
| 5,617,952 A | 4/1997 | Kranendonk |
| 5,630,825 A | 5/1997 | de la Torre et al. |
| 5,632,746 A | 5/1997 | Middleman et al. |
| 5,643,295 A | 7/1997 | Yoon |
| 5,645,552 A | 7/1997 | Sherts |
| 5,649,961 A | 7/1997 | McGregor et al. |
| 5,665,096 A | 9/1997 | Yoon |
| 5,665,109 A | 9/1997 | Yoon |
| 5,669,490 A | 9/1997 | Colligan et al. |
| 5,674,229 A | 10/1997 | Tovey et al. |
| 5,674,230 A | 10/1997 | Tovey et al. |
| 5,693,071 A | 12/1997 | Gorecki et al. |
| 5,707,379 A | 1/1998 | Fleenor et al. |
| 5,709,693 A | 1/1998 | Taylor |
| 5,713,910 A | 2/1998 | Gordon et al. |
| 5,728,107 A | 3/1998 | Zlock et al. |
| 5,728,108 A | 3/1998 | Griffiths et al. |
| 5,733,293 A | 3/1998 | Scirica et al. |
| 5,741,277 A | 4/1998 | Gordon et al. |
| 5,755,729 A | 5/1998 | de la Torre et al. |
| 5,759,188 A | 6/1998 | Yoon |
| 5,766,186 A | 6/1998 | Faraz et al. |
| 5,766,196 A | 6/1998 | Griffiths |
| 5,776,186 A | 7/1998 | Uflacker |
| 5,792,135 A | 8/1998 | Madhani et al. |
| 5,792,151 A | 8/1998 | Heck et al. |
| 5,797,927 A | 8/1998 | Yoon |
| 5,814,054 A | 9/1998 | Kortenbach et al. |
| 5,814,069 A | 9/1998 | Schulze et al. |
| 5,817,084 A | 10/1998 | Jensen |
| 5,846,254 A | 12/1998 | Schulze et al. |
| 5,860,992 A | 1/1999 | Daniel et al. |
| 5,865,836 A | 2/1999 | Miller |
| 5,871,488 A | 2/1999 | Tovey et al. |
| 5,878,193 A | 3/1999 | Wang et al. |
| 5,897,563 A | 4/1999 | Yoon et al. |
| 5,908,428 A | 6/1999 | Scirica et al. |
| 5,911,727 A | 6/1999 | Taylor |
| 5,938,668 A | 8/1999 | Scirica et al. |
| 5,941,430 A | 8/1999 | Kuwabara |
| 5,947,982 A | 9/1999 | Duran |
| 5,954,731 A | 9/1999 | Yoon |
| 5,954,733 A | 9/1999 | Yoon |
| 5,993,466 A | 11/1999 | Yoon |
| 6,016,905 A | 1/2000 | Gemma et al. |
| 6,053,908 A | 4/2000 | Crainich et al. |
| 6,056,771 A | 5/2000 | Proto |
| 6,071,289 A | 6/2000 | Stefanchik et al. |
| 6,086,601 A | 7/2000 | Yoon |
| 6,096,051 A | 8/2000 | Kortenbach et al. |
| 6,126,666 A | 10/2000 | Trapp et al. |
| 6,129,741 A | 10/2000 | Wurster et al. |
| 6,135,385 A | 10/2000 | Martinez de Lahidalga |
| 6,136,010 A | 10/2000 | Modesitt et al. |
| 6,138,440 A | 10/2000 | Gemma |
| 6,152,934 A | 11/2000 | Harper et al. |
| 6,214,030 B1 | 4/2001 | Matsutani et al. |
| 6,231,565 B1 | 5/2001 | Tovey et al. |
| 6,332,888 B1 | 12/2001 | Levy et al. |
| 6,332,889 B1 | 12/2001 | Sancoff et al. |
| 6,364,888 B1 | 4/2002 | Niemeyer et al. |
| 6,443,962 B1 | 9/2002 | Gaber |
| 6,454,778 B2 | 9/2002 | Kortenbach |
| 6,719,763 B2 | 4/2004 | Chung et al. |
| 6,719,764 B1 | 4/2004 | Gellman et al. |
| 6,743,239 B1 | 6/2004 | Kuehn et al. |
| 6,755,843 B2 | 6/2004 | Chung et al. |
| 6,783,524 B2 | 8/2004 | Anderson et al. |
| 6,783,537 B1 | 8/2004 | Kuhr et al. |
| 6,923,819 B2 | 8/2005 | Meade et al. |
| 6,936,054 B2 | 8/2005 | Chu |
| 6,939,358 B2 | 9/2005 | Palacios et al. |
| 6,955,643 B2 | 10/2005 | Gellman et al. |
| 7,004,951 B2 † | 2/2006 | Gibbens |
| 7,041,111 B2 | 5/2006 | Chu |
| 7,131,979 B2 | 11/2006 | DiCarlo et al. |
| 7,144,401 B2 | 12/2006 | Yamamoto et al. |
| 7,232,447 B2 | 6/2007 | Gellman et al. |
| 7,235,087 B2 | 6/2007 | Modesitt et al. |
| 7,338,504 B2 | 3/2008 | Gibbens, III et al. |
| 7,442,198 B2 | 10/2008 | Gellman et al. |
| 7,520,382 B2 | 4/2009 | Kennedy et al. |
| 7,524,320 B2 | 4/2009 | Tierney et al. |
| 7,582,096 B2 | 9/2009 | Gellman et al. |
| 7,588,583 B2 | 9/2009 | Hamilton et al. |
| 7,615,060 B2 | 11/2009 | Stokes et al. |
| 7,628,796 B2 | 12/2009 | Shelton, IV et al. |
| 7,637,369 B2 | 12/2009 | Kennedy et al. |
| 7,666,194 B2 | 2/2010 | Field et al. |
| 7,686,831 B2 | 3/2010 | Stokes et al. |
| 7,691,098 B2 | 4/2010 | Wallace et al. |
| 7,703,653 B2 | 4/2010 | Shah et al. |
| 7,763,036 B2 | 7/2010 | Stokes et al. |
| 7,766,925 B2 | 8/2010 | Stokes et al. |
| 7,770,365 B2 | 8/2010 | Enriquez, III et al. |
| 7,806,891 B2 | 10/2010 | Nowlin et al. |
| 7,815,654 B2 | 10/2010 | Chu |
| 7,824,401 B2 | 11/2010 | Manzo et al. |
| 7,828,812 B2 | 11/2010 | Stokes et al. |

(56) References Cited

U.S. PATENT DOCUMENTS

| | | |
|---|---|---|
| 7,833,235 B2 | 11/2010 | Chu |
| 7,833,236 B2 | 11/2010 | Stokes et al. |
| 7,842,048 B2 | 11/2010 | Ma |
| 7,846,169 B2 | 12/2010 | Shelton, IV et al. |
| 7,862,572 B2 † | 1/2011 | Meade |
| 7,862,582 B2 | 1/2011 | Ortiz et al. |
| 7,887,554 B2 | 2/2011 | Stokes et al. |
| 7,891,485 B2 | 2/2011 | Prescott |
| 7,896,890 B2 | 3/2011 | Ortiz et al. |
| 7,935,128 B2 | 5/2011 | Rioux et al. |
| 7,942,886 B2 | 5/2011 | Alvarado |
| 7,947,052 B2 | 5/2011 | Baxter, III et al. |
| 7,976,553 B2 | 7/2011 | Shelton, IV et al. |
| 7,976,555 B2 | 7/2011 | Meade et al. |
| 7,993,354 B1 | 8/2011 | Brecher et al. |
| 8,012,161 B2 | 9/2011 | Primavera et al. |
| 8,016,840 B2 | 9/2011 | Takemoto et al. |
| 8,048,092 B2 | 11/2011 | Modesitt et al. |
| 8,057,386 B2 | 11/2011 | Aznoian et al. |
| 8,066,737 B2 | 11/2011 | Meade et al. |
| 8,100,922 B2 | 1/2012 | Griffith |
| 8,118,820 B2 | 2/2012 | Stokes et al. |
| 8,123,762 B2 | 2/2012 | Chu et al. |
| 8,123,764 B2 | 2/2012 | Meade et al. |
| 8,136,656 B2 | 3/2012 | Kennedy et al. |
| 8,187,288 B2 | 5/2012 | Chu et al. |
| 8,196,739 B2 | 6/2012 | Kirsch |
| 8,206,284 B2 | 6/2012 | Aznoian et al. |
| 8,211,143 B2 | 7/2012 | Stefanchik et al. |
| 8,236,010 B2 | 8/2012 | Ortiz et al. |
| 8,236,013 B2 | 8/2012 | Chu |
| 8,246,637 B2 | 8/2012 | Viola et al. |
| 8,252,008 B2 | 8/2012 | Ma |
| 8,256,613 B2 | 9/2012 | Kirsch et al. |
| 8,257,369 B2 | 9/2012 | Gellman et al. |
| 8,257,371 B2 | 9/2012 | Hamilton et al. |
| 8,292,067 B2 | 10/2012 | Chowaniec et al. |
| 8,292,906 B2 | 10/2012 | Taylor et al. |
| 8,307,978 B2 | 11/2012 | Kirsch et al. |
| 8,361,089 B2 | 1/2013 | Chu |
| 8,366,725 B2 | 2/2013 | Chu |
| 8,372,090 B2 | 2/2013 | Wingardner et al. |
| 8,398,660 B2 | 3/2013 | Chu et al. |
| 8,460,320 B2 | 6/2013 | Hirzel |
| 8,469,973 B2 | 6/2013 | Meade et al. |
| 8,490,713 B2 | 7/2013 | Furnish et al. |
| 8,500,756 B2 | 8/2013 | Papa et al. |
| 8,512,243 B2 | 8/2013 | Stafford |
| 8,518,058 B2 | 8/2013 | Gellman et al. |
| 8,551,122 B2 | 10/2013 | Lau |
| 8,556,069 B2 | 10/2013 | Kirsch |
| 8,623,048 B2 | 1/2014 | Brecher et al. |
| 8,641,728 B2 | 2/2014 | Stokes et al. |
| 8,663,253 B2 | 3/2014 | Saliman |
| 8,696,687 B2 | 4/2014 | Gellman et al. |
| 8,702,729 B2 | 4/2014 | Chu |
| 8,709,021 B2 | 4/2014 | Chu et al. |
| 8,746,445 B2 | 6/2014 | Kennedy et al. |
| 8,747,304 B2 | 6/2014 | Zeiner et al. |
| 8,771,295 B2 | 7/2014 | Chu |
| 8,821,518 B2 | 9/2014 | Saliman et al. |
| 8,821,519 B2 | 9/2014 | Meade et al. |
| 8,920,440 B2 | 12/2014 | McClurg et al. |
| 8,920,441 B2 | 12/2014 | Saliman |
| 2002/0193809 A1 | 12/2002 | Meade et al. |
| 2003/0208100 A1 | 11/2003 | Levy |
| 2003/0233104 A1 | 12/2003 | Gellman et al. |
| 2004/0050721 A1 | 3/2004 | Roby et al. |
| 2004/0172047 A1 | 9/2004 | Gellman et al. |
| 2005/0015101 A1 | 1/2005 | Gibbens, III et al. |
| 2005/0216038 A1 | 9/2005 | Meade et al. |
| 2006/0036232 A1 | 2/2006 | Primavera et al. |
| 2006/0047309 A1 | 3/2006 | Cichocki |
| 2006/0069396 A1 | 3/2006 | Meade et al. |
| 2006/0111732 A1 | 5/2006 | Gibbens et al. |
| 2006/0173491 A1 | 8/2006 | Meade et al. |
| 2006/0281970 A1 | 12/2006 | Stokes et al. |
| 2006/0282096 A1 | 12/2006 | Papa et al. |
| 2006/0282097 A1 | 12/2006 | Ortiz et al. |
| 2006/0282098 A1 | 12/2006 | Shelton, IV et al. |
| 2006/0282099 A1 | 12/2006 | Stokes et al. |
| 2007/0088372 A1 | 4/2007 | Gellman et al. |
| 2007/0162052 A1 | 7/2007 | Hashimoto et al. |
| 2007/0173864 A1 | 7/2007 | Chu |
| 2007/0256945 A1 | 11/2007 | Kennedy et al. |
| 2008/0091220 A1 | 4/2008 | Chu |
| 2008/0103357 A1 | 5/2008 | Zeiner et al. |
| 2008/0109015 A1 | 5/2008 | Chu et al. |
| 2008/0132919 A1 | 6/2008 | Chui et al. |
| 2008/0228204 A1 | 9/2008 | Hamilton et al. |
| 2008/0243146 A1 | 10/2008 | Sloan et al. |
| 2008/0255590 A1 | 10/2008 | Meade et al. |
| 2009/0024145 A1 | 1/2009 | Meade et al. |
| 2009/0205987 A1 | 8/2009 | Kennedy et al. |
| 2009/0209980 A1 | 8/2009 | Harris |
| 2009/0259092 A1 | 10/2009 | Ogdahl et al. |
| 2009/0287226 A1 | 11/2009 | Gellman et al. |
| 2009/0312772 A1 | 12/2009 | Chu |
| 2010/0016866 A1 | 1/2010 | Meade et al. |
| 2010/0023024 A1 | 1/2010 | Zeiner et al. |
| 2010/0036415 A1 | 2/2010 | Cabezas |
| 2010/0042116 A1 | 2/2010 | Chui et al. |
| 2010/0063519 A1 | 3/2010 | Park et al. |
| 2010/0078336 A1 | 4/2010 | Reyhan et al. |
| 2010/0100125 A1 | 4/2010 | Mahadevan |
| 2010/0152751 A1 | 6/2010 | Meade et al. |
| 2010/0274265 A1 | 10/2010 | Wingardner et al. |
| 2011/0028999 A1 | 2/2011 | Chu |
| 2011/0040308 A1 | 2/2011 | Cabrera et al. |
| 2011/0042245 A1 | 2/2011 | McClurg et al. |
| 2011/0046642 A1 | 2/2011 | McClurg et al. |
| 2011/0046667 A1 | 2/2011 | Culligan et al. |
| 2011/0060352 A1 | 3/2011 | Chu |
| 2011/0082476 A1 | 4/2011 | Furnish et al. |
| 2011/0288582 A1 | 11/2011 | Meade et al. |
| 2011/0295278 A1 | 12/2011 | Meade et al. |
| 2011/0313433 A1 | 12/2011 | Woodard, Jr. et al. |
| 2012/0004672 A1 | 1/2012 | Giap et al. |
| 2012/0035626 A1 | 2/2012 | Chu |
| 2012/0041456 A1 | 2/2012 | Gellman et al. |
| 2012/0055828 A1 | 3/2012 | Kennedy et al. |
| 2012/0059396 A1 | 3/2012 | Harris et al. |
| 2012/0109163 A1 | 5/2012 | Chu et al. |
| 2012/0123471 A1 | 5/2012 | Woodard, Jr. et al. |
| 2012/0130404 A1 | 5/2012 | Meade et al. |
| 2012/0143248 A1 | 6/2012 | Brecher et al. |
| 2012/0150199 A1 | 6/2012 | Woodard, Jr. et al. |
| 2012/0165838 A1 | 6/2012 | Kobylewski et al. |
| 2012/0215234 A1 | 8/2012 | Chowaniec et al. |
| 2012/0226292 A1 | 9/2012 | Hirzel |
| 2012/0228163 A1 | 9/2012 | Kirsch |
| 2012/0232567 A1 | 9/2012 | Fairneny |
| 2012/0283748 A1 | 11/2012 | Ortiz et al. |
| 2012/0283750 A1 | 11/2012 | Saliman et al. |
| 2012/0283755 A1 | 11/2012 | Gellman et al. |
| 2013/0041388 A1 | 2/2013 | Lane et al. |
| 2013/0282027 A1 | 10/2013 | Woodard, Jr. et al. |
| 2013/0282031 A1 | 10/2013 | Woodard, Jr. et al. |
| 2013/0331866 A1 | 12/2013 | Gellman et al. |
| 2014/0088621 A1 | 3/2014 | Krieger et al. |
| 2014/0166514 A1 | 6/2014 | Martin et al. |
| 2014/0171970 A1 | 6/2014 | Martin et al. |
| 2014/0171971 A1 | 6/2014 | Martin et al. |
| 2014/0171972 A1 | 6/2014 | Martin |
| 2014/0171975 A1 | 6/2014 | Martin et al. |
| 2014/0171976 A1 | 6/2014 | Martin et al. |
| 2014/0171977 A1 | 6/2014 | Martin et al. |
| 2014/0171978 A1 | 6/2014 | Martin |

(56) References Cited

U.S. PATENT DOCUMENTS

| | | | |
|---|---|---|---|
| 2014/0171979 | A1 | 6/2014 | Martin et al. |
| 2014/0172015 | A1 | 6/2014 | Martin et al. |
| 2015/0127024 | A1 | 5/2015 | Berry |

FOREIGN PATENT DOCUMENTS

| | | |
|---|---|---|
| EP | 0739184 B1 | 9/1998 |
| EP | 1791476 A2 | 6/2007 |
| EP | 2292157 A2 | 3/2011 |
| EP | 2308391 A1 | 4/2011 |
| FR | 2540377 A1 | 2/1984 |
| GB | 18602 A | 0/1909 |
| GB | 2389313 A | 12/2003 |
| JP | 55-151956 | 11/1980 |
| WO | WO 9519149 A1 | 7/1995 |
| WO | WO 9729694 A1 | 8/1997 |
| WO | WO 9912482 A1 | 3/1999 |
| WO | WO 9940850 A1 | 8/1999 |
| WO | WO 9947050 A2 | 9/1999 |
| WO | WO 0112084 A1 | 2/2001 |
| WO | WO 02102226 A2 | 12/2002 |
| WO | WO 03028541 A2 | 4/2003 |
| WO | WO 2004012606 A1 | 2/2004 |
| WO | WO 2004021894 A1 | 3/2004 |
| WO | WO 2006034209 A2 | 3/2006 |
| WO | WO 2007089603 A2 | 8/2007 |
| WO | WO 2008045333 A2 | 4/2008 |
| WO | WO 2008045376 A2 | 4/2008 |
| WO | WO 2008/081474 A1 | 7/2008 |
| WO | WO 2008147555 A2 | 12/2008 |
| WO | WO 2010062380 A2 | 6/2010 |
| WO | WO 2012044998 A2 | 4/2012 |
| WO | WO 2012/068002 A1 | 5/2012 |
| WO | WO 2013/142487 A1 | 9/2013 |
| WO | WO 2014/162434 A1 | 10/2014 |

OTHER PUBLICATIONS

U.S. Appl. No. 13/792,976, filed Mar. 11, 2013 by Ethicon Endo-Surgery, Inc.
U.S. Appl. No. 13/793,048, filed Mar. 11, 2013 by Ethicon Endo-Surgery, Inc.
U.S. Appl. No. 29/493,229, filed Jun. 6, 2014 by Ethicon Endo-Surgery, Inc.
U.S. Appl. No. 29/493,231, filed Jun. 6, 2014 by Ethicon Endo-Surgery, Inc.
U.S. Appl. No. 14/297,993, filed Jun. 6, 2014 by Ethicon Endo-Surgery, Inc.
U.S. Appl. No. 14/298,005, filed Jun. 6, 2014 by Ethicon Endo-Surgery, Inc.
U.S. Appl. No. 14/298,015, filed Jun. 6, 2014 by Ethicon Endo-Surgery, Inc.
U.S. Appl. No. 14/298,028, filed Jun. 6, 2014 by Ethicon Endo-Surgery, Inc.
U.S. Appl. No. 14/298,038, filed Jun. 6, 2014 by Ethicon Endo-Surgery, Inc.
U.S. Appl. No. 14/298,056, filed Jun. 6, 2014 by Ethicon Endo-Surgery, Inc.
U.S. Appl. No. 14/298,072, filed Jun. 6, 2014 by Ethicon Endo-Surgery, Inc.
U.S. Appl. No. 14/298,083, filed Jun. 6, 2014 by Ethicon Endo-Surgery, Inc.
U.S. Appl. No. 14/600,486, filed Jan. 20, 2015 by Ethicon Endo-Surgery, Inc.
U.S. Appl. No. 29/493,233, filed Jun. 6, 2014 by Ethicon Endo-Surgery, Inc.
Co-pending U.S. Appl. No. 13/832,595, filed Mar. 15, 2013 by Ethicon Endo-Surgery, Inc.
Co-pending U.S. Appl. No. 13/832,660, filed Mar. 15, 2013 by Ethicon Endo-Surgery, Inc.
Co-pending U.S. Appl. No. 13/832,709, filed Mar. 15, 2013 by Ethicon Endo-Surgery, Inc.
Co-pending U.S. Appl. No. 13/832,816, filed Mar. 15, 2013 by Ethicon Endo-Surgery, Inc.
Co-pending U.S. Appl. No. 13/832,867, filed Mar. 15, 2013 by Ethicon Endo-Surgery, Inc.
Co-pending U.S. Appl. No. 13/832,897, filed Mar. 15, 2013 by Ethicon Endo-Surgery, Inc.
Co-pending U.S. Appl. No. 13/832,986, filed Mar. 15, 2013 by Ethicon Endo-Surgery, Inc.
Co-pending U.S. Appl. No. 13/833,042, filed Mar. 15, 2013 by Ethicon Endo-Surgery, Inc.
Co-pending U.S. Appl. No. 13/833,121, filed Mar. 15, 2013 by Ethicon Endo-Surgery, Inc.
Pages from www.endoevolution.com. Printed on Jun. 3, 2014, but publication date unknown. Please treat as prior art until applicant establishes otherwise.
Covidien Brochure Endo Stitch, Suturing Made Easy Features and Benefits, 2008 4 Pages.
Endoevolution, LLC. Endo 360, Laparoscopic & Minimally Invasive Suturing Devices Catalog, 2011, 2 Pages.
U.S. Appl. No. 14/688,497, filed Apr. 16, 2015 by Ethicon Endo-Surgery, Inc.
U.S. Appl. No. 14/721,244, filed May 26, 2015 by Ethicon Endo-Surgery, Inc.
U.S. Appl. No. 14/721,251, filed May 26, 2015 by Ethicon Endo-Surgery, Inc.
International Search Report Dated May 6, 2014, International Application No. PCT/US2013/074866.
U.S. Appl. No. 14/741,849, filed Jun. 17, 2015 by Ethicon Endo-Surgery, Inc.
U.S. Appl. No. 29/530,605, filed Jun. 18, 2015 by Ethicon Endo-Surgery, Inc.
International Preliminary Report Dated Jun. 16, 2015, International Application No. PCT/US2013/074866.
International Search Report Dated Sep. 15, 2015, International Application No. PCT/US2015/031883.
International Search Report Dated Sep. 28, 2015, International Application No. PCT/US2015/031911.
European Search Report Dated Dec. 7, 2015; Application No. 15176796.9.
European Search Report Dated Dec. 4, 2015; Application No. 15176924.7.
European Search Report Dated Nov. 30, 2015; Application No. 15176774.6.

† cited by third party

CIRCULAR NEEDLE APPLIER WITH OFFSET NEEDLE AND CARRIER TRACKS

RELATED APPLICATIONS

This application claims the benefit of provisional application 61/736,678 filed 13 Dec. 2012, provisional application 61/736,682 filed 13 Dec. 2012, provisional application 61/736,690 filed 13 Dec. 2012, and provisional application 61/736,696 filed 13 Dec. 2012, the contents of which are incorporated herein by reference.

BACKGROUND

The present invention relates in general to surgical devices and procedures, and more particularly to surgical suturing.

Sutures are often used in a wide variety of surgical procedures. Manual suturing is typically accomplished by the surgeon using a fine pair of pliers to grab and hold a suture needle, pierce the tissue with the needle, let go of the needle, and regrasp the needle to pull the needle and accompanying suture thread through the tissues to be sutured. Such needles are typically curved with the suture attached to the trailing end of the needle. A variety of automated suturing devices have been attempted to speed the process of suturing and to facilitate fine suturing or suturing during endoscopic, laparoscopic or arthroscopic surgeries. While automated suturing devices are generally known, no one has previously made or used a surgical suturing device in accordance with the present invention.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, the figures are not necessarily drawn to scale, but rather to illustrate the principles of the invention.

SUMMARY

Figure 1:
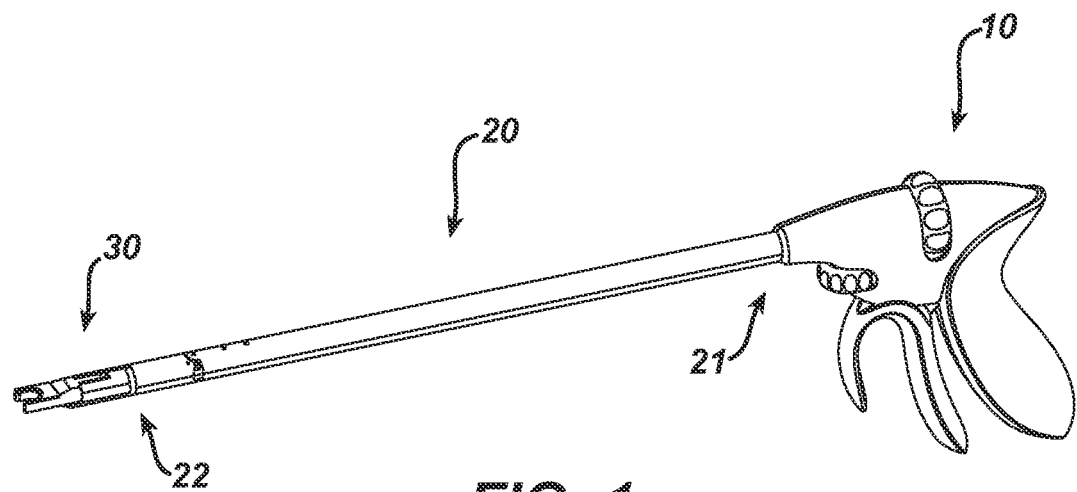
FIG. 1 depicts a perspective view of a surgical suturing device.

In one embodiment, a surgical suturing device has an elongate shaft having a proximal end, a distal end, and a longitudinal axis between the proximal and distal ends. An actuator is connected to the proximal end of the elongate shaft. A circular needle applier is connected to the distal end of the elongate shaft. The elongate shaft articulates proximal of the circular needle applier and the circular needle applier rotates about the longitudinal axis.

The actuator may comprise a manual handle. The handle may comprise a first input to selectively actuate the circular needle applier. The surgical device may further comprise a second input to selectively articulate the shaft. The surgical device may further comprise a third input to selectively rotate the circular needle applier about the longitudinal axis. The elongate shaft may articulate about a joint. The circular needle applier may rotate about a bearing.

In another embodiment, a surgical suturing device has an elongate shaft has a proximal end, a distal end, and a longitudinal axis between the proximal and distal ends. An actuator is connected to the proximal end of the elongate shaft. A circular needle applier is on the distal end of the elongate shaft. The circular needle applier has an arced needle and a needle driver operatively connected to the actuator to rotate the arced needle in a circular path. A joint is positioned between the proximal and distal ends of the elongate shaft. The joint is operatively connected to the actuator to selectively articulate the shaft. A bearing is on the shaft positioned distally of the joint. The bearing is operatively connected to the actuator to selectively rotate the circular needle applier about the longitudinal axis.

In another embodiment, a surgical suturing device comprises an elongate shaft having a proximal end, a distal end, and a longitudinal axis between the proximal and distal ends. An actuator is connected to the proximal end of the elongate shaft. A circular needle applier is connected to the distal end of the elongate shaft. A means articulates the elongate shaft, and a means rotates the circular needle applier about the longitudinal axis. The surgical suturing device may further comprise a means to actuate the circular needle applier.

In another embodiment, a surgical suturing system comprises a reusable shaft and actuator. A disposable cartridge comprises a surgical needle, a length of suture connected to the surgical needle, and a needle driver operative to engage and move the needle relative the cartridge. The disposable cartridge may further comprise a transmission operatively connected to the needle driver. The reusable shaft and actuator may be autoclavable. The reusable shaft and actuator is reusable for at least 50 operations. The reusable shaft and actuator is reusable for at least 150 operations. The reusable shaft and actuator is reusable for at least 200 operations.

In another embodiment, a surgical suturing system comprises a reusable shaft having a proximal end and a distal end, the distal end has a receiver and a rotary drive. A reusable actuator is connected to the proximal end of the shaft. A disposable cartridge is adapted to be attached to and detached from the receiver. The cartridge comprises an arced track, an arced needle positioned in the track having a leading end and a trailing end, a length of suture connected to the trailing end, a reciprocating needle driver operative to engage and move the needle in the arced circular track, and a transmission operatively connected to the needle driver having a rotary input adapted to couple to the rotary drive. The reusable shaft and actuator may be autoclavable.

In another embodiment, a disposable surgical needle cartridge is adapted to be attached to and detached from a surgical suturing device. The disposable cartridge comprises an arced needle track, an arced needle positioned in the needle track having a leading end and a trailing end, a length of suture connected to the needle, a reciprocating needle driver operative to engage and move the needle in the needle track, a transmission operatively connected to the needle driver, and a torsional interface adapted to couple the transmission to a rotary drive in the surgical suturing device. The reciprocating needle driver and transmission are completely encased in the cartridge. The surgical suturing device may be reusable. The surgical suturing device may comprise an elongate shaft with a proximal end, a distal end, and a receiver adapted to interface with the cartridge. The disposable surgical needle cartridge may further comprise a surgical suturing device.

In another embodiment, a surgical suturing system comprises a shaft having a proximal end, a distal end, a longitudinal axis between the proximal and distal ends, and receiver on the distal end with a rotary drive. A cartridge is selectively attachable to and detachable from the receiver. The cartridge has a surgical needle, a length of suture connected to the needle, a needle driver operative to engage and move the needle relative the cartridge, a transmission operatively connected to the needle driver, and a torsional interface rotationally coupling the rotary drive to the transmission.

The rotary drive may deliver a torque to the transmission through the torsional interface about an axis transverse to the longitudinal axis of the shaft. The rotary drive may deliver a torque through the torsional interface about an axis perpendicular to the longitudinal axis of the shaft. The rotary drive may comprise a rack and pinion. The receiver may comprise a distally extending arm axially off-set from the longitudinal axis of the shaft. The arm may comprise a medially facing deck. The rotary drive may be positioned at least partially in the arm.

The surgical suturing system may further comprise a second distally extending arm axially off-set from the longitudinal axis of the shaft, the arms defining a space dimensioned and adapted to receive the cartridge. The surgical suturing system may further comprise a latch operable to lock and unlock the cartridge to the receiver. The cartridge may be attached to and detached from the receiver by longitudinally sliding the cartridge relative to the receiver.

In another embodiment, a surgical suturing system comprises a shaft having a proximal end, a distal end, and a longitudinal axis between the proximal and distal ends. A receiver is on the distal end of the shaft. The receiver has a pair of distally extending arms defining a space. A cartridge is selectively attachable to and detachable from the receiver by longitudinally sliding the cartridge in the space. The cartridge has a surgical needle, a length of suture connected to the needle, a needle driver operative to engage and move the needle relative the cartridge. A latch selectively locks and unlocks the cartridge in the receiver.

The surgical suturing system may further comprise a rotary drive positioned at least partially in one of the arms. The surgical suturing system may further comprise a transmission in the cartridge operatively connected to the needle driver, and a torsional interface rotationally coupling the rotary drive to the transmission.

In another embodiment, a surgical suturing system comprises a shaft having a proximal end, a distal end, a longitudinal axis between the proximal and distal ends, and receiver on the distal end with a rotary drive. A cartridge is selectively attachable to and detachable from the receiver. The cartridge has a surgical needle, a length of suture connected to the needle, a needle driver operative to engage and move the needle relative the cartridge, and a transmission operatively connected to the needle driver. A means rotationally couples the rotary drive to the transmission. The surgical suturing system may further comprise a means for attaching and detaching the cartridge to the receiver. The surgical suturing system may further comprise a means for locking and unlocking the cartridge in the receiver.

In another embodiment, a surgical suturing device comprises an arced needle track. An arced needle is positioned in the needle track, the needle having a leading end, a trailing end, a medial face, and a lateral face. A length of suture is connected to the needle. An arced carrier track is spaced from the needle track. A reciprocating needle driver has a carrier positioned in the carrier track and a driver positioned in the needle track and is operative to engage and move the needle in the needle track. A transmission is operative to reciprocate the carrier in the carrier track.

The surgical suturing device may further comprise a wall separating the carrier track from the needle track. The surgical suturing device may further comprise a slotted opening through the wall, the slot communicating between the carrier track and the needle track. The needle driver may extend through the slotted opening and into the needle track. The slotted opening may be adjacent the medial edge of the arced needle track. The slotted opening may be adjacent the lateral edge of the arced needle track. The arced needle track and arced carrier track may be co-axial. The needle track and carrier track may be off-set along the shared axis from one another. The needle track and carrier track may be co-radial. The needle may further comprise steps dimensioned and adapted to be engaged by the driver. The steps may be on the medial face of the needle. The steps may be on the lateral face of the needle.

In another embodiment, a surgical suturing device comprises an arced needle track. An arced needle is positioned in the needle track. The needle has a leading end, a trailing end, a medial face, and a lateral face. A length of suture is connected to the needle. An arced carrier track is off-set along a shared axis with the arced needle track. A wall separates the arced needle track from the arced carrier track. The wall has a slotted opening communicating between the arced carrier track and the arced needle track. A reciprocating needle driver has a carrier positioned in the arced carrier track and a driver positioned in the arced needle track operative to engage and move the needle in the needle track. A transmission is operative to reciprocate the carrier in the carrier track.

In another embodiment, a surgical suturing device comprises an arced needle track, an arced needle positioned in the needle track, and a length of suture connected to needle. A reciprocating needle driver is operative to engage and move the needle in the needle track. A rotary input rotates about an axis. A link has a proximal end connected to the rotary input and a distal end connected to the needle driver. Rotation of the rotary input in a first angular direction translates the needle driver in a second angular direction opposite of the first angular direction.

The link may further comprise a longitudinal slot interposed between the proximal and distal ends, the longitudinal slot receiving a pin about which the link both longitudinally translated and pivots. The distal end may be pivotally connected to the needle driver. The connection between the needle driver and link distal end may translate in an arced path having a first radius. The proximal end of the link may connect to the rotary input at a second radius from the torsion drive axis, and the first radius may be greater than the second radius. The rotary input, link, and needle driver may have no indeterminate point. The rotary input may comprise a radial slot receiving a pin connected to the proximal end of the link. The surgical suturing device of may further comprise an elongate shaft having a proximal end and a distal end, an actuator connected to the shaft proximal end, a rotary drive operably connected to the actuator, and a torsional interface rotationally coupling the rotary driver to the rotary input. The rotary drive may comprise a rack and pinion. The rotary input may have a reciprocating rotational motion. The needle driver may reciprocate at least 180 degrees in an arced track. The needle driver may rotate the needle in a circular path at least partially defined by the needle track. The rotary input and needle may rotate in parallel planes.

In another embodiment, a surgical suturing device comprises a needle having a leading end, a trailing end, and an arced body between the leading and trailing ends. A length of suture is connected to the needle. A needle driver is adapted to engage and rotate the needle in a circular path in a first rotational direction. A pawl is adapted to engage the trailing end of the needle to prevent the needle from rotating in a second rotational direction opposite of the first rotational direction.

The needle may be rotated in a plane, and the pawl may resiliently deflect at an angle transverse to the plane. The pawl may resiliently deflect substantially perpendicular to the plane. The needle may be rotated in a plane, and the pawl may resiliently deflect substantially in the plane. The pawl may be positioned laterally from the needle. The pawl may be positioned medially from the needle. The pawl may have a first end about which the pawl pivots, and a second end having an edge that engages the trailing end of the needle. The surgical suturing device may further comprise a second pawl adapted to engage the trailing end of the needle to prevent the needle from rotating in a second rotational direction opposite of the first rotational direction. The pawls may be antipodal to one another along the circular path. The trailing end may comprise a barrel receiving the suture, the barrel having a trailing face circumscribing the suture and the pawl may engage the trailing face to prevent the needle from rotating in a second rotational direction opposite of the first rotational direction. The pawl may translates along a path perpendicular to the needle path, and the pawl may further comprise a spring biasing the pawl in the needle path. The pawl may further comprise a ramp adapted to be engaged by the needle to deflect the pawl out of the needle path and allow the needle to pass the pawl. The pawl may translate along a path transverse a plane defined by the circular needle path.

In another embodiment, a surgical suturing device comprises a needle having a leading end, a trailing end, an arced body between the leading and trailing ends, and two steps located at antipodal positions on the body. A length of suture is connected to the needle. A needle driver reciprocates at least 180 degrees between a driven position and a returned position. The needle driver is adapted to engage the needle steps to rotate the needle in a circular path in first rotational direction. A pawl is positioned adjacent the driven position of the needle driver. The pawl is adapted to engage the needle steps to prevent the needle from rotating in a second rotational direction opposite of the first rotational direction.

The surgical device may further comprise a spring biasing the pawl in the needle path. The pawl may further comprise a ramp adapted to be engaged by the needle and the needle driver to deflect the pawl out of the needle path and allow the needle and needle driver to pass the pawl. The pawl may deflect in a plane defined by the circular needle path. The pawl may have a first end about which the pawl pivots, a second end having an edge that engages the needle steps, and a spring biasing the second end into the needle path. In the driven position the needle driver may be interposed between the pawl and the needle. The surgical device may further comprise a second a pawl positioned adjacent the returned position of the needle driver, the second pawl adapted to engage the needle steps to prevent the needle from rotating in a second rotational direction opposite of the first rotational direction.

In another embodiment, a surgical suturing device comprises a needle having a leading end, a trailing end, an arced body between the leading and trailing ends, and two steps located at antipodal positions on the body. A length of suture is connected to the needle. A needle driver reciprocates at least 180 degrees between a driven position and a returned position. The needle driver is adapted to engage the needle steps to rotate the needle in a circular path in first rotational direction. A pawl is positioned adjacent the returned position of the needle driver. The pawl is adapted to engage the needle steps to prevent the needle from rotating in a second rotational direction opposite of the first rotational direction.

The surgical device may further comprise a spring biasing the pawl in the needle path. The pawl may further comprise a proximal ramp adapted to be engaged by the needle and the needle driver to deflect the pawl out of the needle path and allow the needle and needle driver to pass the pawl. The pawl may further comprise a distal ramp adapted to be engaged by the needle driver to deflect the pawl out of the needle path and allow the needle driver to pass the pawl. The distal ramp may be positioned below the needle path. The pawl may deflect in a plane defined by the circular needle path.

In another embodiment, a surgical suturing device comprises a needle having a leading end, a trailing end, an arced body between the leading and trailing ends, and two steps located at antipodal positions on the body. A length of suture connected to the needle. A needle driver reciprocates at least 180 degrees between a driven position and a returned position. The needle driver is adapted to engage the needle steps to rotate the needle in a circular path in first rotational direction. A means engages the needle steps to prevent the needle from rotating in a second rotational direction opposite of the first rotational direction. The means may comprise a pawl. The means may comprise a leaf spring.

In another embodiment, a surgical needle for use in a circular needle applier comprises a leading end, a trailing end, and an arced body between the leading and trailing ends. The body has a medial face and a lateral face. A plurality of steps on the body are adapted to be engaged by a circular needle applier. The steps are formed by plastically deforming the body without removing material. A length of suture is connected to the trailing end.

The steps may be on the medial face. The steps may be on the lateral face. The steps may be formed by a pressing operation. The steps may be formed by a rolling operation. The plurality of steps may comprise two antipodal steps. The body may have an angular span of at least 180 degrees. The arced body may comprise a substantially constant nominal radius about an origin.

In another embodiment, a surgical needle for use in a circular needle applier comprises a leading end has a taper, a trailing end has a barrel, and an arced body extending between the taper and barrel. The body has a medial face, a lateral face, and plurality of steps adapted to be engaged by a circular needle applier. The body has a substantially constant cross sectional area between the taper and barrel. A length of suture is connected in the barrel.

The steps may be on the medial face. The plurality of steps may consist of two antipodal steps on the medial face. The steps may be on the lateral face. The plurality of steps may consist of two antipodal steps on the lateral face. The steps may be formed without removing material from the body. The steps may be formed by a pressing operation. The steps may be formed by a rolling operation. The plurality of steps may comprise two antipodal steps. The body may have an angular span of at least 180 degrees.

In another embodiment, a surgical needle for use in a circular needle applier comprises a distal leading end, a proximal trailing end, and an arced body between the leading and trailing ends. The body has a medial face and a lateral face. A first step on the body is adapted to be engaged by a circular needle applier. The first step is positioned distally from the leading end. A longitudinal flat extends proximally from the first step. The flat defines a generally D-shaped cross sectional shape in the body. A second step on the body is adapted to be engaged by a circular needle applier. The second step is positioned about 180 degrees from the first step. A length of suture is connected to the trailing end.

The needle may have an angular span from the leading end to the trailing end between about 210 degrees and about 270 degrees. The first and second steps may be located on the medial face. The first and second steps may be located on the lateral face. The arced body may comprise a substantially constant nominal radius about an origin. The nominal radius may be between about 0.170 inches to about 0.210 inches. The flat may extend proximally from the first step between about 20 degrees and about 40 degrees. The flat may extend proximally from the first step between about 100 degrees and about 150 degrees. The body may further comprise a ramped portion on the proximal end of the flat such that the cross sectional shape in the body transitions from a generally D-shape to a generally circular shape. The body may further comprise a second longitudinal flat extending proximally from the second step, the second flat defining a generally D-shaped cross sectional shape in the body. The second flat may extend proximally from the second step between about 8 degrees and about 30 degrees. The body may further comprise a ramped portion on the proximal end of the second flat such that the sectional shape in the body transitions from a generally D-shape to a generally circular shape. The leading end may comprise a taper and the trailing end may have a barrel, and the body may have a substantially constant cross sectional area between the taper and barrel.

In another embodiment, packaging for a surgical needle comprises a cartridge having a surgical needle and a needle driver operative to engage and move the needle relative the cartridge. The packaging has a bobbin, and a length of suture connected to the needle and wound around the bobbin. The packaging may further comprise an outer shell enclosing the cartridge, bobbin, and suture. The outer shell may comprise a sheet of material folded over the cartridge and bobbin. The packaging may further comprise a platform resiliently holding the cartridge. The bobbin may be a rotating spool. The cartridge may comprise a pair of arms defining a generally U-shaped distal end, and the packaging may have a block interposed between the arms. The packaging may further comprise a housing and a top sheet enclosing the enclosing the cartridge, bobbin, and suture.

In another embodiment, packaging for a surgical needle a housing and a cartridge releasably held in the housing. The cartridge has a surgical needle and a needle driver operative to engage and move the needle relative the cartridge. A bobbin is in the housing. A length of suture is connected to the needle and wound around the bobbin. The cartridge, bobbin, and suture may be enclosed within the housing. The cartridge may comprise a pair of arms defining a generally U-shaped distal end, and the packaging may further comprise a block attached to the housing and extending between the arms. The housing may define a gap and the cartridge may be positioned at least partially in the gap.

In another embodiment, packaging for a surgical needle comprises a housing having a gap. A cartridge is releasably held in the housing and extends into the gap. The cartridge has a surgical needle, a needle driver operative to engage and move the needle relative the cartridge, and a pair of arms defining a generally U-shaped distal end. A block is attached to the housing and extends between the arms. A rotary spool is in the housing. A length of suture is connected to the needle and wound around the spool. The cartridge, bobbin, and suture are enclosed within the housing.

DETAILED DESCRIPTION

FIG. 1 illustrates an embodiment of a surgical suturing device. An elongate shaft (20) has a proximal end (21), a distal end (22), and a longitudinal axis extending there between. An actuator (10) is connected to the proximal end (21) of the shaft (20). In this embodiment the actuator (10) is a manual pistol grip handle; however, a variety of other manual actuators could also be used, including a scissor grip handle, a syringe grip handle, endoscopic rotary knobs, and the like. The actuator (10) could also take the form of a robotic interface, such as an DAVINCI puck, a housing comprising gears or pulleys, servomechanisms, and the like.

A circular needle applier (30) is connected to the distal end (22) of the shaft (20). The circular needle applier (30) rotates an arced needle in a circular path enabling a surgeon to selectively apply sutures. The circular needle applier (30) may be integral with the shaft (20) and actuator (10) as a unitary disposable instrument intended for a single surgical procedure. The circular needle applier (30) may also be integral with the shaft (20) and actuator (10) as a reusable instrument. Optionally, the circular needle applier (30) may be embodied in a disposable cartridge, and the shaft (20) and actuator (10) may also be disposable. In another variation, the circular needle applier (30) may be embodied in a disposable cartridge, and the shaft (20) and actuator (10) may be reusable. Embodiments with reusable components are intended to be cleaned, sterilized, and reused for a multiple surgical procedures. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also used with low temperature sterilization techniques known in the art.

Figure 2:
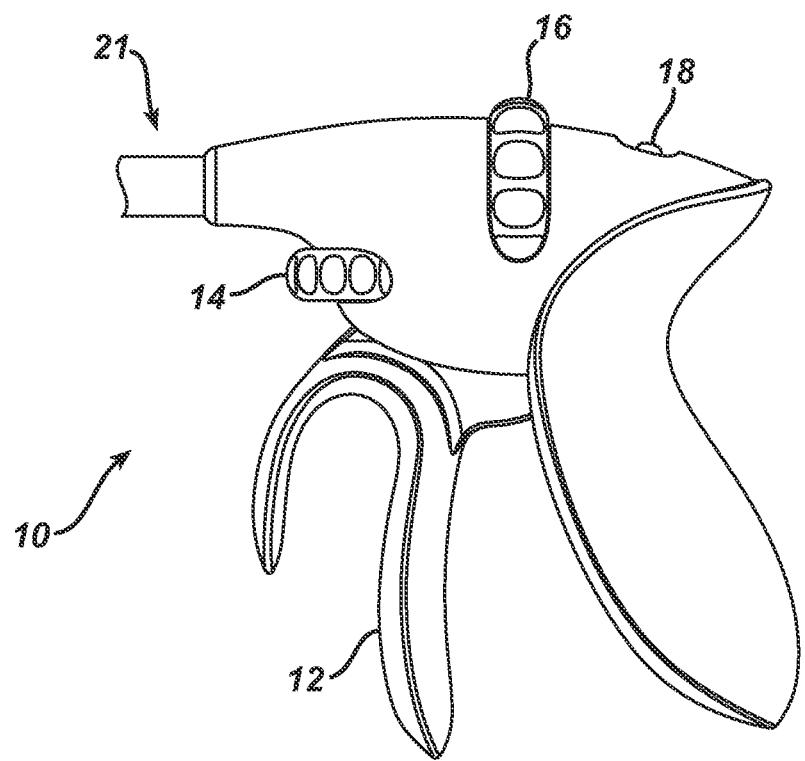
FIG. 2 depicts a side view of an actuator for a surgical suturing device.

FIG. 2 illustrates one embodiment of a manual actuator (10). A first input (12), shown here as a trigger that pivots between an opened and closed position, may be used to selectively actuate the circular needle applier (30). The trigger may be spring biased to return the trigger to its open position. A second input (14), shown here as a rotary knob, may be used to selectively articulate the shaft (20). A third input (16), shown here as a rotary knob, may be used to selectively rotate the circular needle applier (30) about the shaft (20). A fourth input (18), shown here as a switch, may be used to selectively attach and detach a circular needle applier (30) to the shaft (20). Naturally, the number, type, configuration, and operation of the inputs (12, 14, 16, and 18) may vary.

Figure 3A:
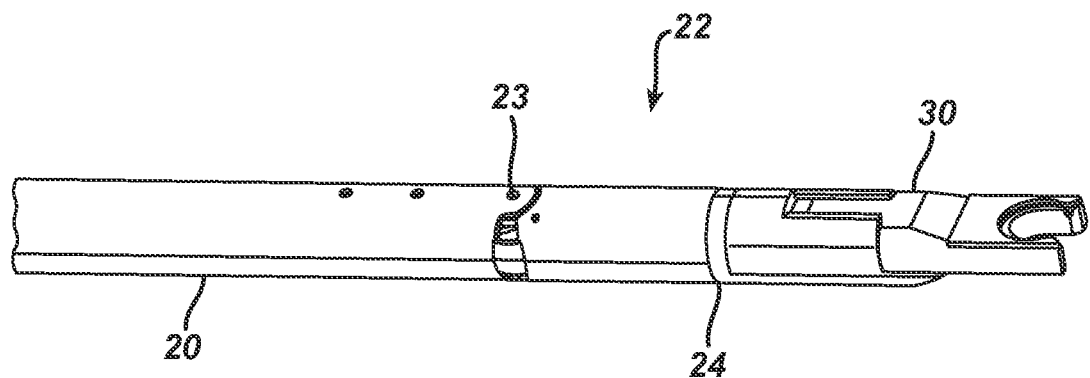
FIG. 3A depicts a perspective view of a shaft in a straight configuration.
Figure 3B:
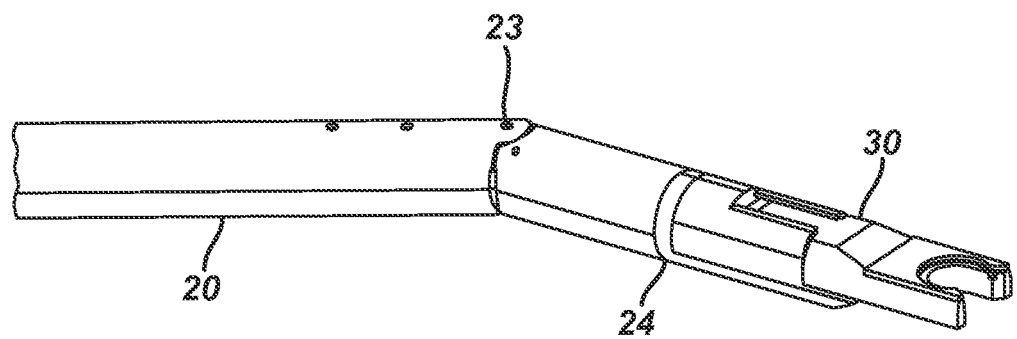
FIG. 3B depicts a perspective view of a shaft in an articulate configuration.
Figure 3C:
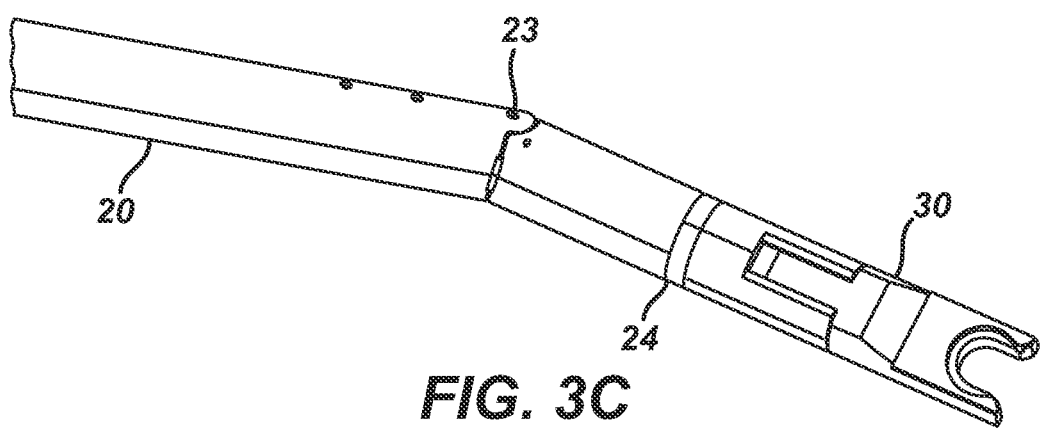
FIG. 3C depicts a perspective view of a shaft in an articulated and rotated configuration.

FIGS. 3A-B illustrate the shaft (20) articulating in response actuation of the second input (14). In this embodiment, the shaft (20) has an articulation joint (23) to facilitate articulation. The shaft (20) includes a bearing (24) positioned distal to the joint (23). FIGS. 3B-C illustrate the circular needle applier (30) rotating at the bearing (24) in response to actuation of the third input (16), even when the shaft (20) is articulated.

Figure 4:
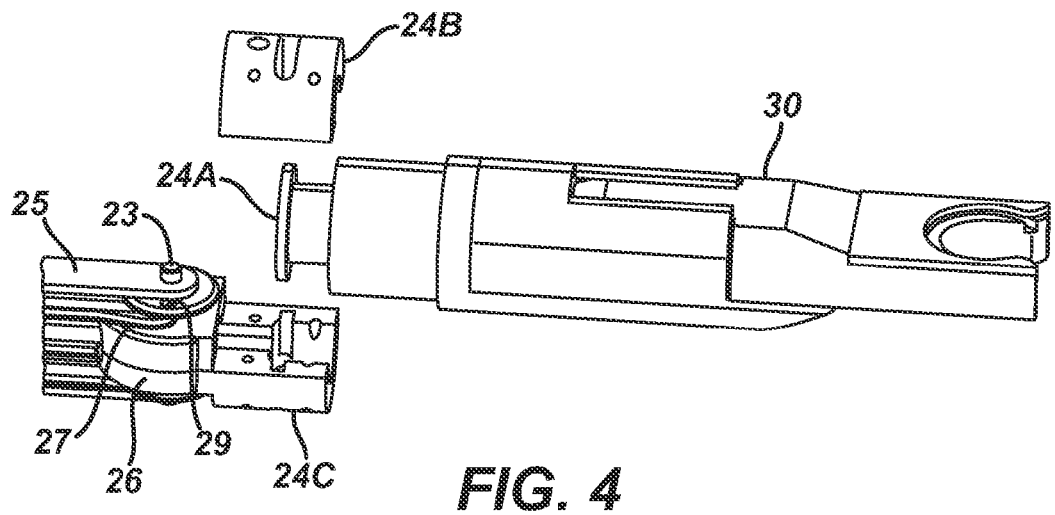
FIG. 4 depicts an exploded view of a shaft bearing.
Figure 5:
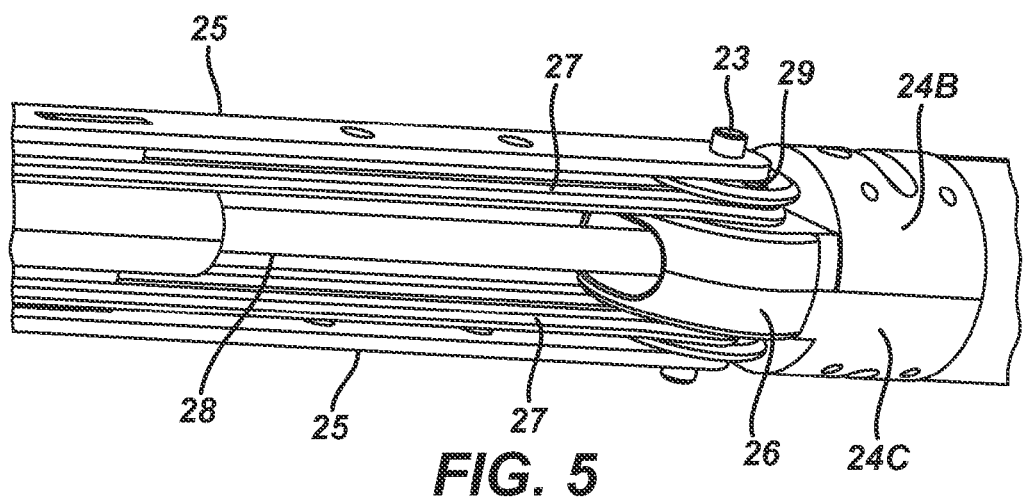
FIG. 5 depicts a partial cut-away view showing the linkages in a shaft.

FIGS. 4-5 illustrate one example of a suitable articulation joint (23) and rotation bearing (24). The bearing (24) includes a circumferential flange (24A) fixed to the circular needle applier (30). The flange (24A) is captured between the bearing supports (24B, 24C) such that the flange (24A) can rotate but prevent axial motion. A flexible co-axial torsion tube (28) passes through the joint (23). The torsion tube (28) has an outer sheath and an inner cable. The outer sheath of the torsion tube (28) is fixed to the flange (24A) and operatively connected to the third input (16). Actuation of the third input (16) will rotate the sheath and in turn rotate circular needle applier (30). The inner cable of the co-axial torsion tube (28) passes through the circumferential flange (24A) and is operatively connected to the first input (12) to provide axial push and pull loads to actuate the circular needle applier (30). Lateral struts (25) support the joint (23) in the shaft (20). A pin (29) connects the rods (27) to the knuckle (26) at a position off-set from the axis of the joint (23). The rods (27) are operatively connected to the second input (14) to push and pull the rods (27) relative the struts (25), which will in turn articulate the shaft (20) about the joint (23).

Figure 6:
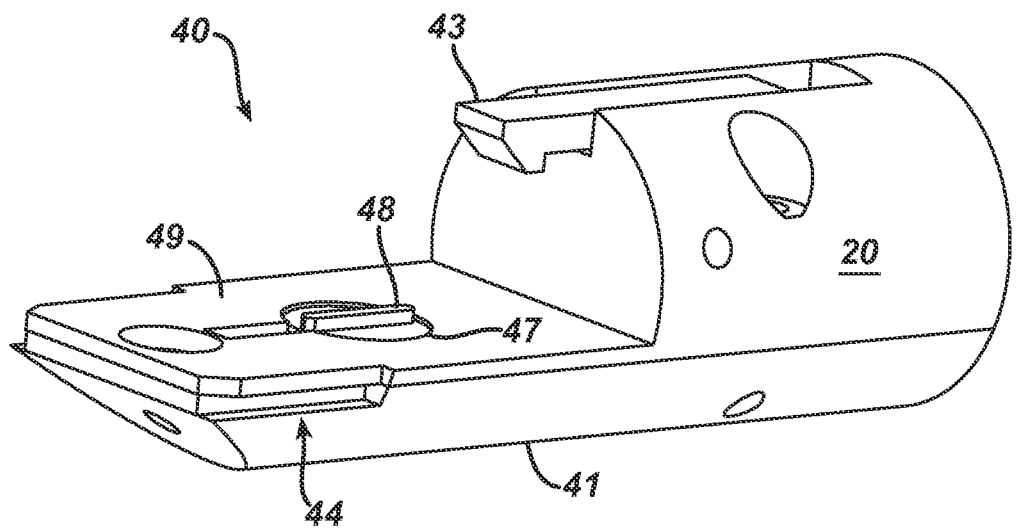
FIG. 6 depicts a perspective view of a cartridge receiver.

FIG. 6 illustrates one example of a receiver (40) located on the distal end (22) of the shaft (20). The receiver (40) is dimensioned and adapted to receive and hold a disposable cartridge containing a circular needle applier (30). The cartridge may contain a surgical needle, a length of suture connected to the surgical needle, a needle driver operative to engage and move the needle relative the cartridge, and a transmission operatively connected to the needle driver. An axially off-set arm (41) extends distally from the shaft (20). The arm (41) has a medially facing deck (49) with a pair of longitudinal slots (44) located below and on either side of the deck (49). A spring loaded latch (43) is adapted to selectively lock and unlock the cartridge to the receiver (40). Optionally, latch (43) may be operatively coupled to the fourth input (18).

Figure 7:
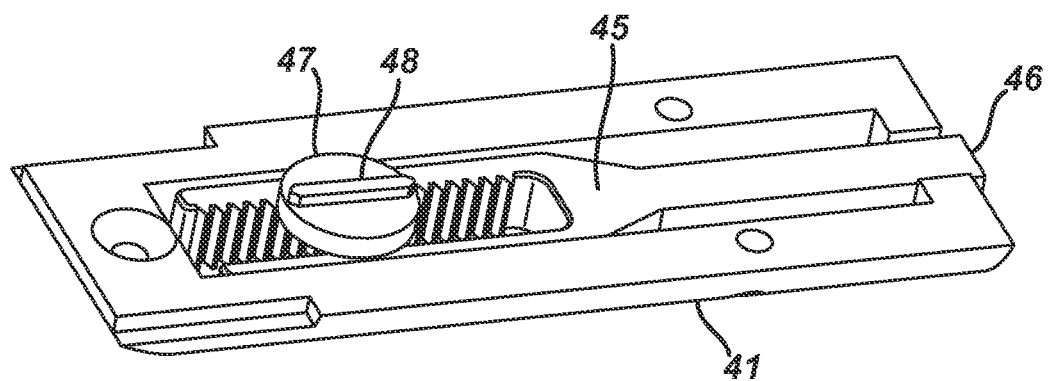
FIG. 7 depicts a perspective view of a rotary drive.

FIG. 7 illustrates a rotary drive having a rack (45) and pinion (47) is positioned partially in the arm (41) and below the deck (49). The inner cable of the co-axial torsion tube (28) is connected to the proximal end (46) of the rack (45) such that closing the trigger of the first input (12) will pull the rack (45) proximally, and opening the trigger of the first input (12), which may be by virtue of a spring return, will push the rack (45) distally. Thus, actuating the first input (12) will rotationally reciprocate the pinion (47). The key (48) translates the reciprocating rotation to the transmission in the cartridge.

Figure 8:
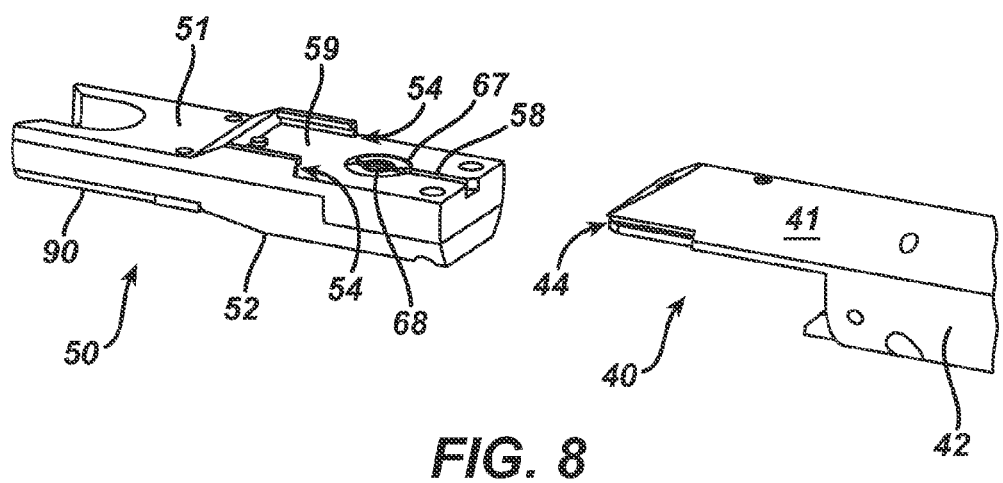
FIG. 8 depicts a perspective view of a cartridge disassembled from a receiver.
Figure 9:
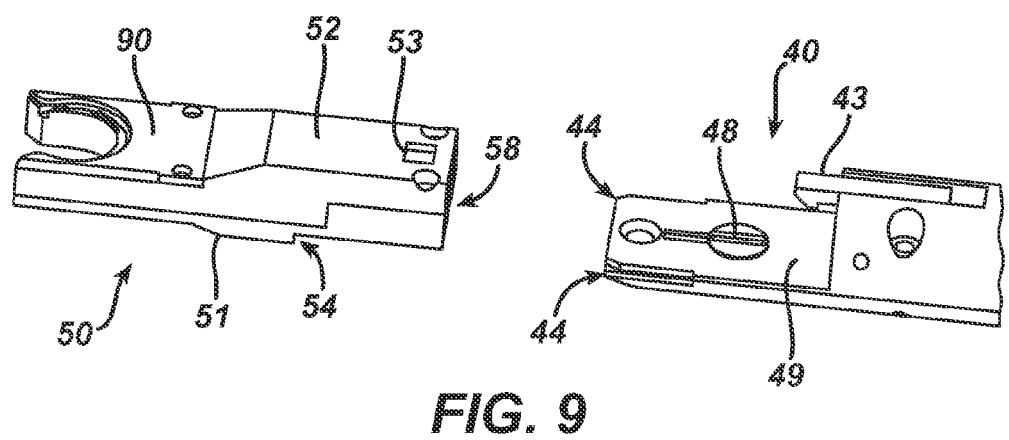
FIG. 9 depicts a perspective view of a cartridge disassembled from a receiver.

FIGS. 8-9 illustrate one example of a disposable cartridge (50) adapted to be attached to the receiver (40). The cartridge (50) may be slid proximally onto the receiver (40) so the two decks (49, 59) are parallel and facing one another until the latch (43) engages the recess (53). The cartridge (50) in encased by a lower housing (51), an upper housing (52), and a needle cover (90). The lower housing (51) has a pair of longitudinal slots (54) dimensioned to interface and mate with the slots (44). The slot (58) is dimensioned to receive the key (48) while the cartridge (50) is being slid onto the receiver (40). When the cartridge (50) is fully seated into the receiver (40), the pinion (47) is axially aligned with rotary input (67), which forms part of the transmission in the cartridge (50), and the key (48) is positioned in the slot (68) thereby providing a torsional interface that rotationally couples the pinion (47) and rotary input (67).

Thus, the rotary drive in the shaft (20) delivers an operational torque to the transmission in the cartridge (50) about an axis perpendicular to the longitudinal axis of the shaft (20). The operational torque could also be delivered along an axis parallel or in line with the longitudinal axis of the shaft (20), or at another transverse angle relative the longitudinal axis of the shaft (20). Further, other torsional interfaces known in the art other than the key (48) and slot (68) embodiment may be used, such as a cross, star, square, spline, and the like.

Figure 10A:
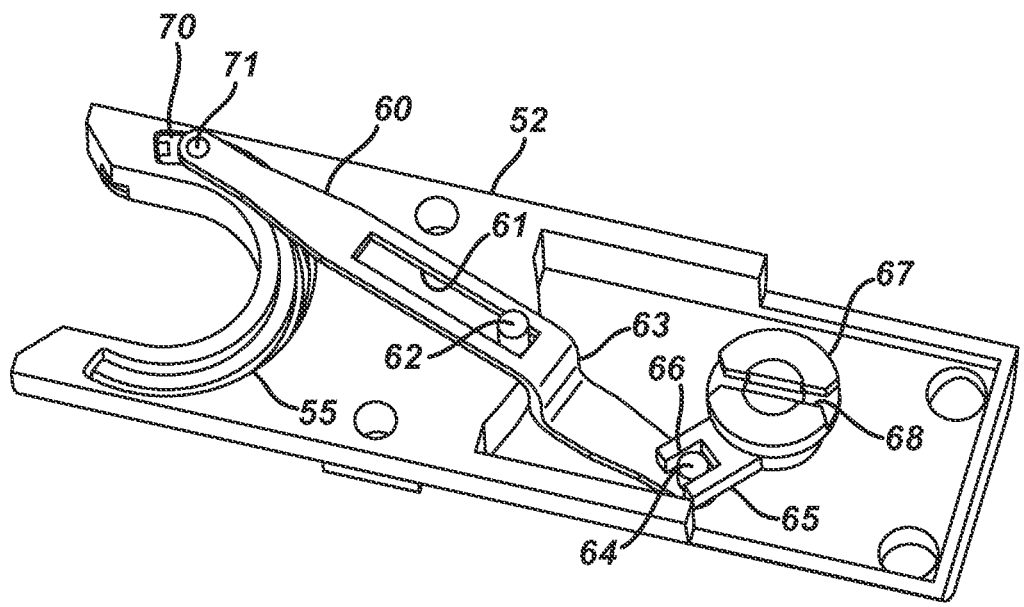
FIG. 10A depicts a perspective view of a transmission for driving a needle at one end of its stroke.
Figure 10B:
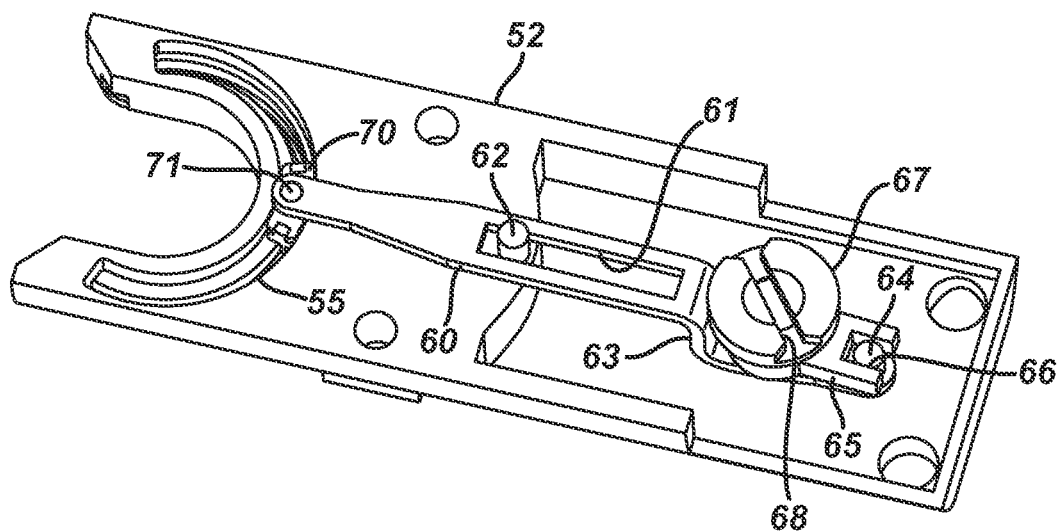
FIG. 10B depicts a perspective view of a transmission for driving a needle at mid-stroke.
Figure 10C:
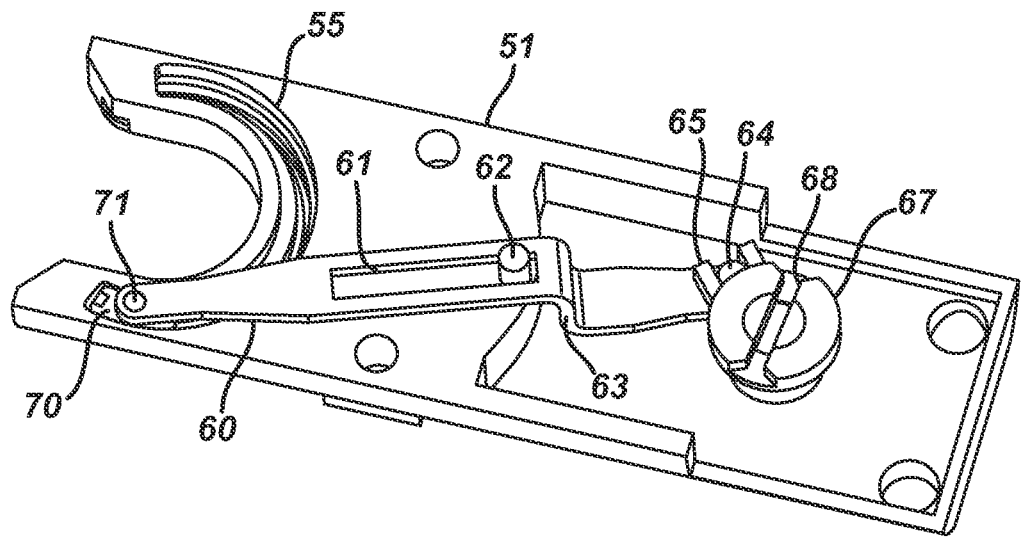
FIG. 10C depicts a perspective view of a transmission for driving a needle at the other end of its stroke.

FIGS. 10A-C illustrate one example of a transmission in the cartridge (50) for driving a needle in a circular path. A needle driver (70) reciprocates in the arced carrier track (55) and is operative to engage and rotate an arced needle. A link (60) connects the rotary input (67) to the needle driver (70). The pin (71) pivotally connects the distal end of the link (60) to the needle driver (70). The rotary input (67) has a slot (68) that mates with the key (48) so as to receive the reciprocating rotation from the rotary drive. The rotary input (67) has a radially extending arm (65) with a radial slot (66). The pin (64) is positioned in the slot (66) connecting the proximal end of the link (60) to the rotary input (67). The slot (66) rotationally constrains the pin (64) to the arm (65) while accommodating some relative radial movement. The link (60) has a longitudinal slot (61) receiving the fixed pin (62) about which the link (60) both longitudinally translates and pivots. The pins (71, 62) are co-planar, but pin (66) lies in an off-set plane. The link (60) includes a bent section (63) to accommodate the off-set. Other than the torsional interface, which in this embodiment comprises the face of the rotary input (67) with the slot (68), the entire transmission is completely encased within cartridge (50).

FIG. 10A illustrates the needle driver (70) positioned at one end of its stroke in the carrier track (55). As shown in FIG. 10B, counterclockwise rotation of the rotary input (67) will translate the needle driver (70) clockwise along the carrier track (55). The radius of rotation of the pin (71) is greater than the radius of rotation of the pin (64). As shown in FIG. 10C, continued counterclockwise rotation of the rotary input (67) will continue to translate the needle driver (70) clockwise until it reaches the other end of its stroke in the carrier track (55). The rotary input (67), link (60), and needle driver (70) have no indeterminate point, so rotation of the rotary input (67) will cause the needle driver (70) to translate in the opposite rotational direction throughout the stroke without binding.

The sequence can be reversed by rotating the rotary input (67) clockwise, which will translate the needle driver (70) counterclockwise in the carrier track (55). Thus, actuation of the first input (12) will cause the needle driver (70) to reciprocate back and forth along the carrier track (55).

Figure 11:
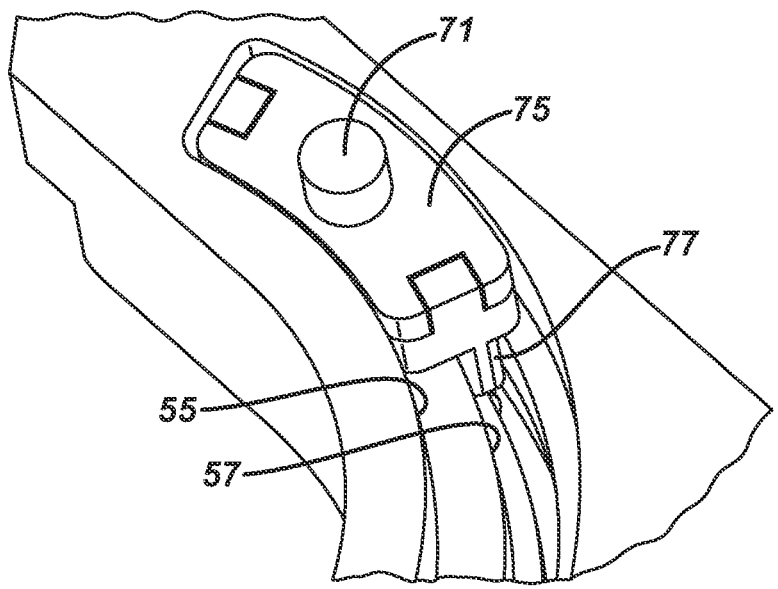
FIG. 11 depicts a perspective view of a needle driver in a carrier track.
Figure 12:
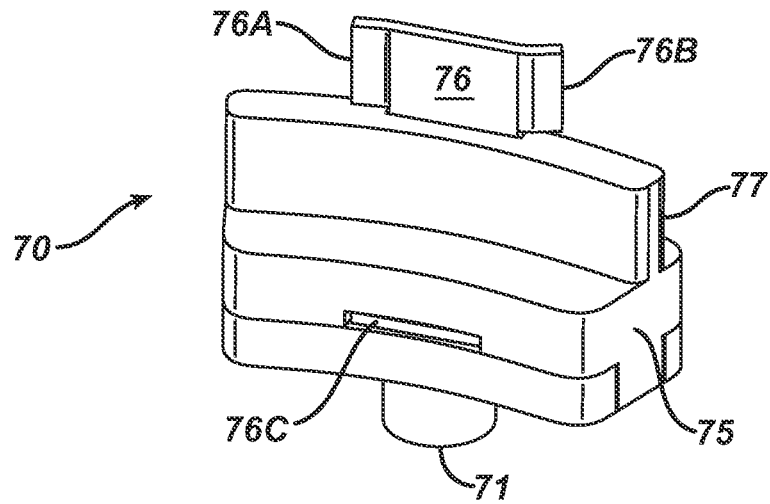
FIG. 12 depicts a perspective view of a needle driver.
Figure 13:
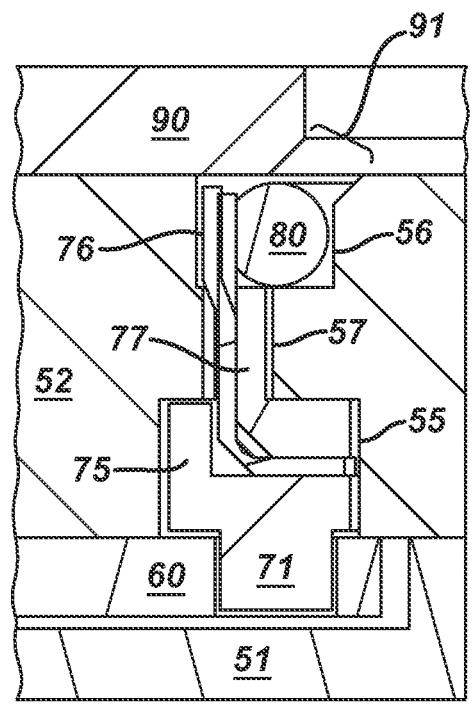
FIG. 13 depicts a cross-sectional view of the needle driver in a carrier track and a needle in a needle track.

FIGS. 11-13 illustrate one example of a needle driver (70) and its operation. The upper housing (52) has an arced needle track (56) and an arced carrier track (55). In this embodiment, the needle track (56) and carrier track (55) each have a nominal radius of curvature originating from a common axis. Therefore, the needle track (56) and carrier track (55) are co-axial. Also in this embodiment, the tracks (55, 56) at least partially overlap one another in the radial dimension, so they are also co-radial. The tracks (55, 56) are off-set along the shared axis from one another with a wall separating the tracks (55, 56). A slot (57) opens through the wall and provides communication between the carrier track (55) and the needle track (56). In this embodiment the slot (57) opens adjacent the lateral edge of the needle track (56).

The needle driver (70) has a carrier (75) dimensioned to slideably fit in the carrier track (55). In this embodiment, the carrier (75) has a curved body matching the arc of the carrier track (55). The pin (71) extends from the carrier (75) to engage the link (60). The needle driver (70) extends through the slot (57) and into the needle track (56). The carrier (75) has a flange (77) dimensioned to fit in the slot (57). A driver (76) is attached to the carrier (75) and is positioned in the needle track and operative to engage and move the needle (80) in the needle track (56). The driver (76) is an L-shaped metal blade with one leg (76C) sandwiched between two pieces that form the carrier (75). The driver (76) may deflect as a cantilevered leaf spring laterally from the flange (77), and may also resiliently bias to engage the lateral face of the needle (80). In this embodiment the driver (76) has a drive face (76A) and a return face (76B). The drive face (76A) has an edge that is operative to engage steps on the needle (80) during the drive stroke. When so engaged, the needle (80) will slide in the needle track (56) in unison with the driver (70). The return face (76B) is ramped to facilitate the driver (76) sliding over the needle (80) on the return stroke.

The lower housing (51) constrains the link (60) to engage the pin (71) and also constrains the carrier (75) in the carrier track (55). The needle cover (90) constrains the needle (80) in the needle track (56). The needle cover (90) also defines a window (91) along the length of the needle track (56). The window (91) is dimensioned to receive the suture. As the needle (80) is rotated in the needle track (56), the suture may extend out through the window (91). However, the window (91) is dimensioned smaller than the needle (80) so as to constrain the needle (80) in the needle track (56).

Figure 14A:
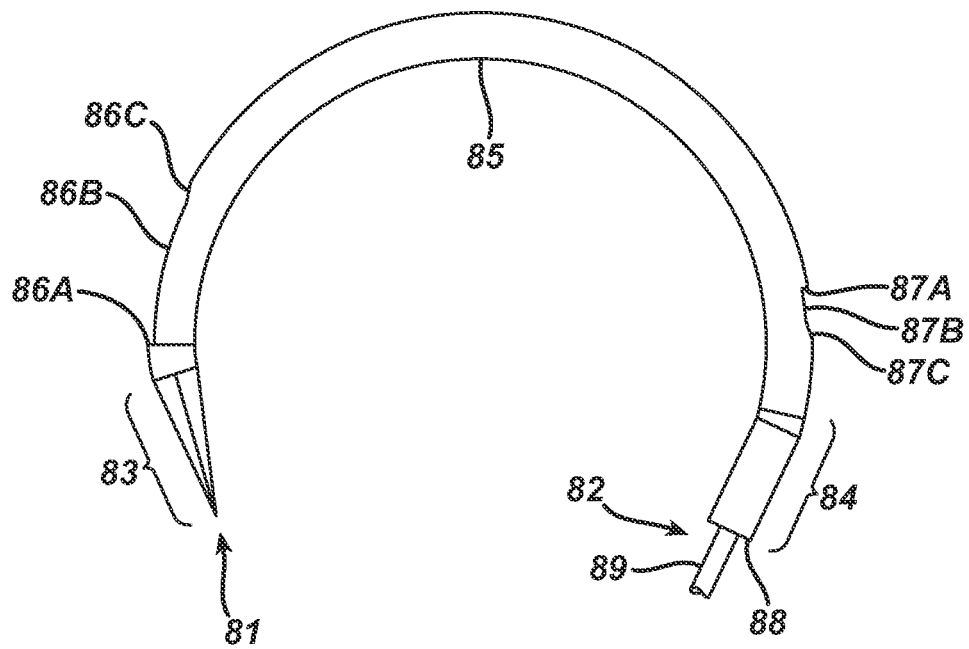
FIG. 14A depicts a plan view of arced needle.
Figure 14B:
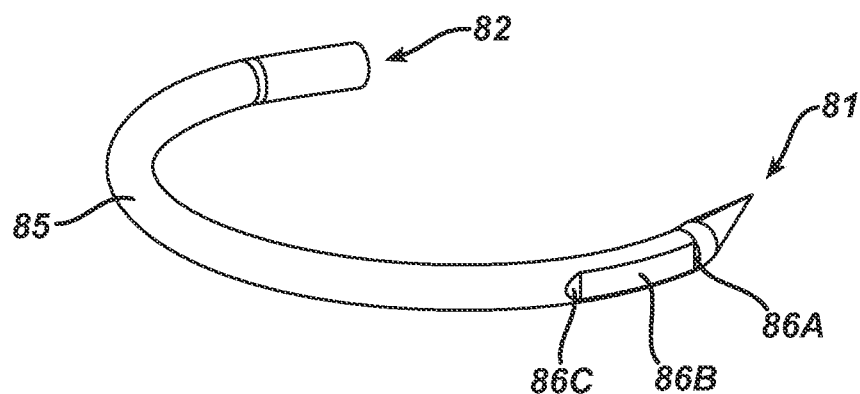
FIG. 14B depicts a perspective view of arced needle.

FIGS. 14A-B illustrates one embodiment of a needle (80) having a distal leading end (81) with a sharp tapered tip (83). A variety of geometries could be employed at the leading end (81), including conical, bladed, blunt, cutting tips, taper-cut tips, and the like. The proximal trailing end (82) has a tubular barrel (84) that fixedly receives a length of suture (89). A trailing face (88) circumscribes the suture (89). A variety of different types of suture (89) may be employed, including braided, monofilament, and barbed suture using a variety of materials, including polyglactin (e.g., VICRYL), poliglecprone (e.g., MONOCRYL), polydioxanone (e.g., PDS), surgical gut, polyester (e.g., ETHIBOND), silk (e.g. PERMA-HAND), polypropylene (e.g., PROLENE), other absorbable or non-absorbable materials, and the like.

The angular span between the leading end (81) and trailing end (82) may be between about 210 degrees and about 270 degrees. An arced body (85) extends between the tapered tip (83) and the barrel (84). The body (85) may arc at a substantially constant radius of curvature. The nominal radius of curvature may be between about 0.170 inches to about 0.210 inches, preferably between about 0.180 inches to about 0.205 inches, and more preferably between about 0.190 inches to about 0.200 inches; however, other dimensions are also possible.

A distal step (86A) is positioned on the lateral face of the body (85). The distal step (86A) may be located between about 20 degrees and about 30 degrees from the leading end (81). A proximal step (87A) is positioned on the lateral face of the body (85). The proximal step (87A) is about 180 degrees from the distal step (86A). Therefore, the steps (86A, 87A) are located at antipodal locations on the needle (80). The steps (86A, 87A) are adapted to be engaged by the driver (76) of the needle driver (70). The height of the steps (86A, 87A) are preferably between about 0.003 inches and about 0.010 inches, but other dimensions are also possible. Flats (86B, 87B) extend distally from the steps (86A, 87A) and define a generally D-shaped cross sectional shape in the body (85). The distal flat (86B) has an angular span between about 20 degrees and about 40 degrees from the distal step (86A). The proximal flat (87B) has an angular span between about 8 degrees and about 30 degrees from the distal step (87A). The flats (86B, 87B) may facilitate reducing the dimensional interference between the needle (80) and driver (76) during the return stroke of the needle driver (70). Ramps (86C, 87C) are located adjacent the proximal ends the flats (86B, 87B) such that the cross-sectional shape of the body (85) transitions from a generally D-shape to a generally circular shape. The ramps (86C, 87C) reduce the likelihood of the driver (76) snagging on the needle (80) during the return stroke of the needle driver (70).

The step, flat, and ramp features (86A, 87A, 86B, 87B, 86C, 87C) may be made by plastically deforming the body (85). For instance, a die can be used in a pressing or rolling operation on a straight wire stock to form the features on the body (85). Then the straight stock can be bent to its arced shape. While the cross-sectional shape of the body (85) will change along its length, the cross-sectional area between the taper (83) and the barrel (84) will remain substantially constant. This is advantageous over notched needle designs where material is being removed to create notches, such as in a cutting or grinding operation, resulting in a weaker needle. Furthermore, plastically forming features in the body (85) is more reliable and reproducible, and capable of faster production.

Figure 15A:
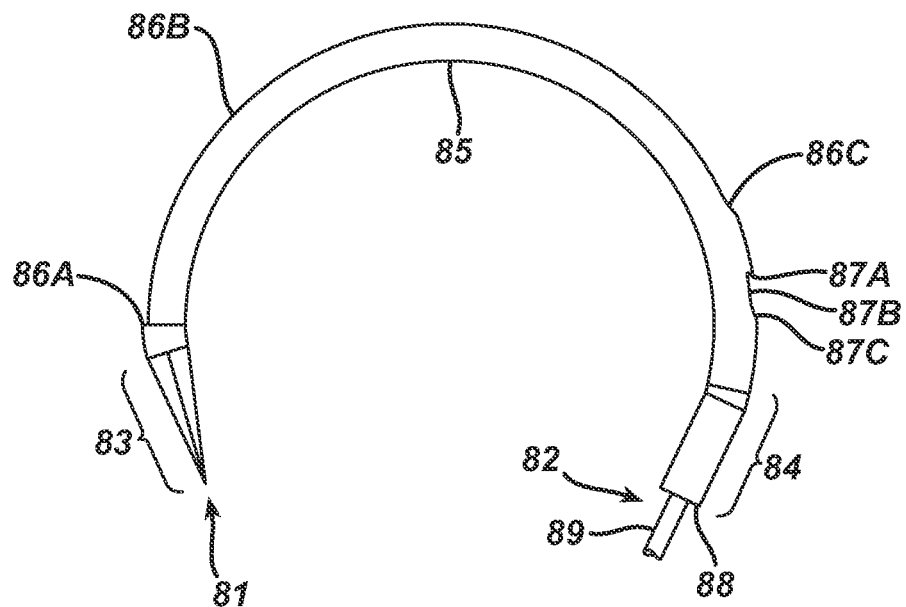
FIG. 15A depicts a plan view of arced needle.
Figure 15B:
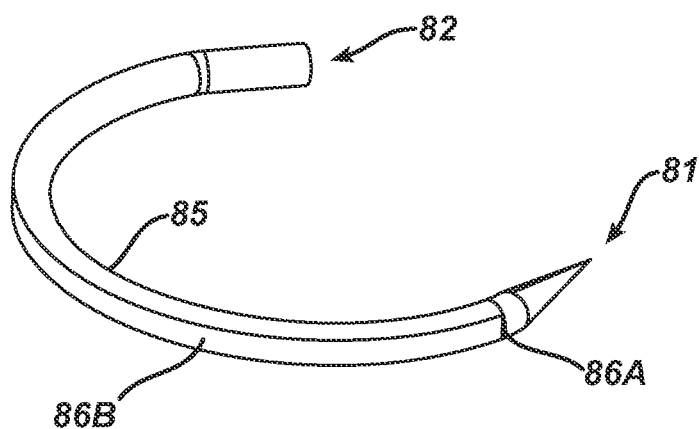
FIG. 15B depicts a perspective view of arced needle.

FIGS. 15A-B illustrates another embodiment of needle (80) substantially the same as in FIGS. 14A-B; however, the distal flat (86B) has an angular span between about 100 degrees and about 150 degrees from the distal step (86A).

FIGS. 16A-D illustrate one embodiment of a circular needle applier (30) rotating an arced needle (80) in a circular path. The suture has been hidden in the figures to better illustrate device operation. A pair of arms (94, 95) define a generally U-shaped distal end on the circular needle applier (30). The needle track (56) has an exit port (92) in arm (94) and an entrance port (93) in arm (95). The leaf springs (96, 97) allow the needle (80) to rotate counterclockwise, but prevent the needle (80) from rotating clockwise. Leaf spring (97) extends into the needle track (56) and resiliently deflects laterally when engaging the lateral face of the needle (80), thus allowing counterclockwise motion. Leaf spring (96) extends into the needle track (56) and resiliently deflects medially when engaging the medial face of the needle (80), thus allowing counterclockwise motion. But when the needle (180) passes one of the leaf springs (96, 97), it will deflect into the path to interfere and engage the trailing face (88), thus preventing the needle (80) from rotating clockwise.

Figure 16A:
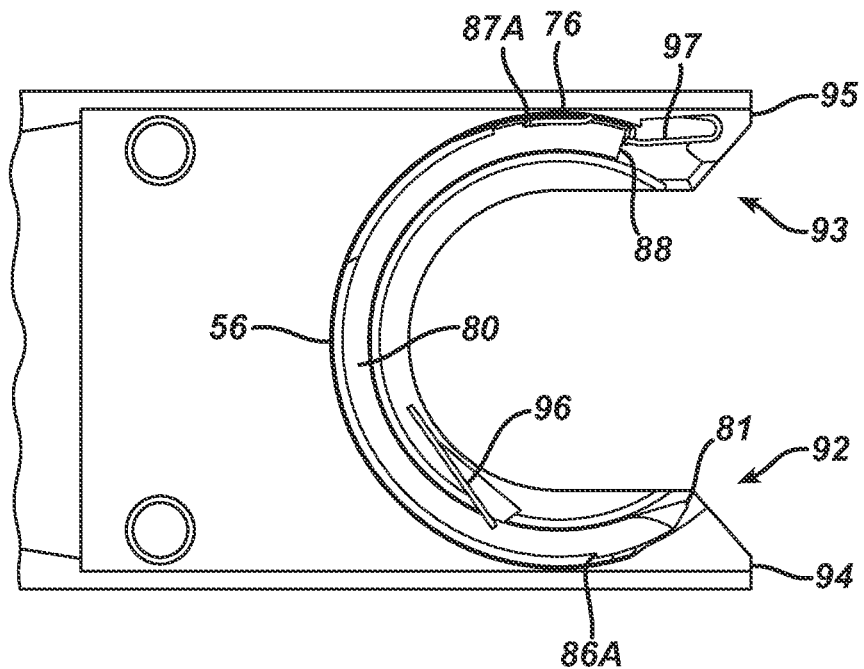
FIG. 16A depicts a plan view of a needle applier with a needle in its retracted position and the needle driver in its returned position.

FIG. 16A shows the device in its initial position. The needle (80) is in its retracted position and completely contained in the needle track (56). The needle driver (70) has a reciprocating stroke between a returned position and a driven position. In this figure, the driver (76) is in its returned position in arm (95). The driver (76) is adjacent the proximal step (87A). Leaf spring (96) resiliently engages the needle (80), while leaf spring (97) is adjacent the trailing face (88) preventing the needle (80) from rotating clockwise.

Figure 16B:
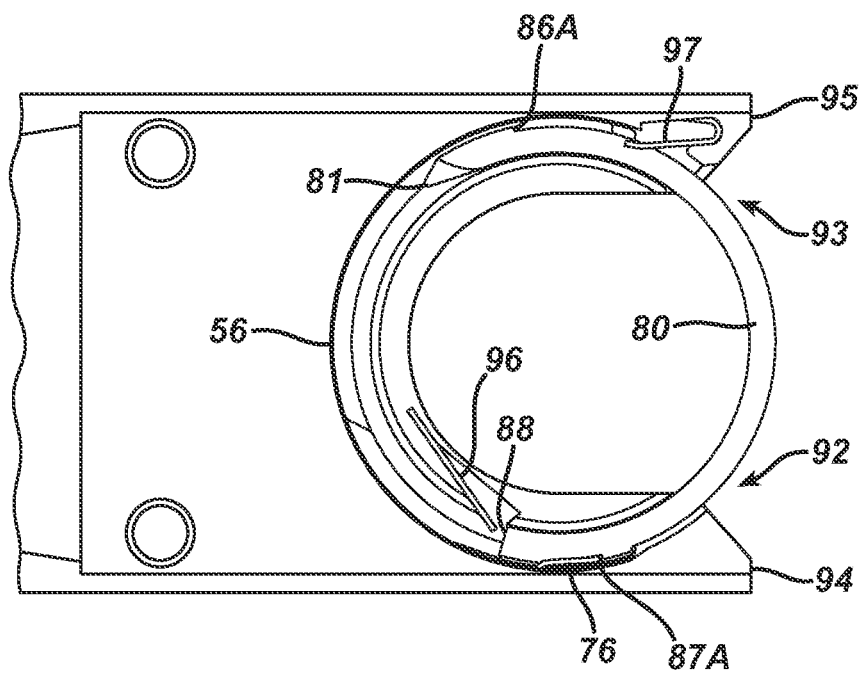
FIG. 16B depicts a plan view of a needle applier with a needle in its extended position and the needle driver in its driven position.

When the first input (12) is depressed closing the trigger, the needle driver (70) will be actuated through its drive stroke where it is rotated at least about 180 degrees counterclockwise to the driven position as shown in FIG. 16B. During the drive stroke, the driver (76) engages the proximal step (87A) and will in unison rotate the needle (80) about 180 degrees to its extended position. The needle (80) will span across the arms (94, 95) between the exit port (92) and the entrance port (93). Tissue interposed between the arms (94, 95) will be pieced by the leading end (81) of the needle (80).

Figure 16C:
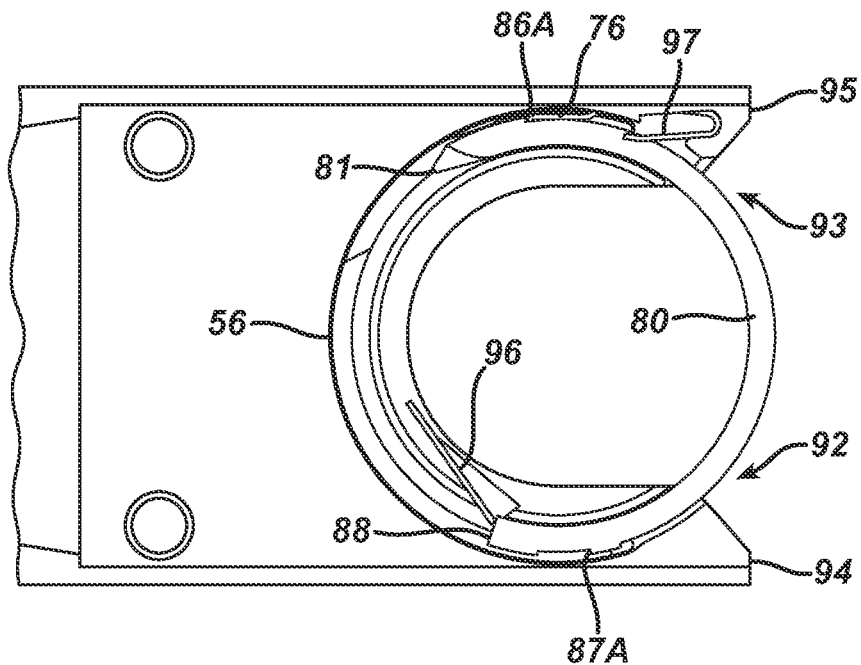
FIG. 16C depicts a plan view of a needle applier with a needle in its extended position and the needle driver in its returned position.

When the first input (12) is released and the spring return opens the trigger, the needle driver (70) reciprocates through its return stroke where it is rotated about 180 degrees clockwise back to the return position shown in FIG. 16C. During the return stroke the driver (76) slides over the needle (80) and the leaf spring (96) engages the trailing face (88) preventing the needle (80) from rotating clockwise. The driver (76) is adjacent the distal step (86A).

Figure 16D:
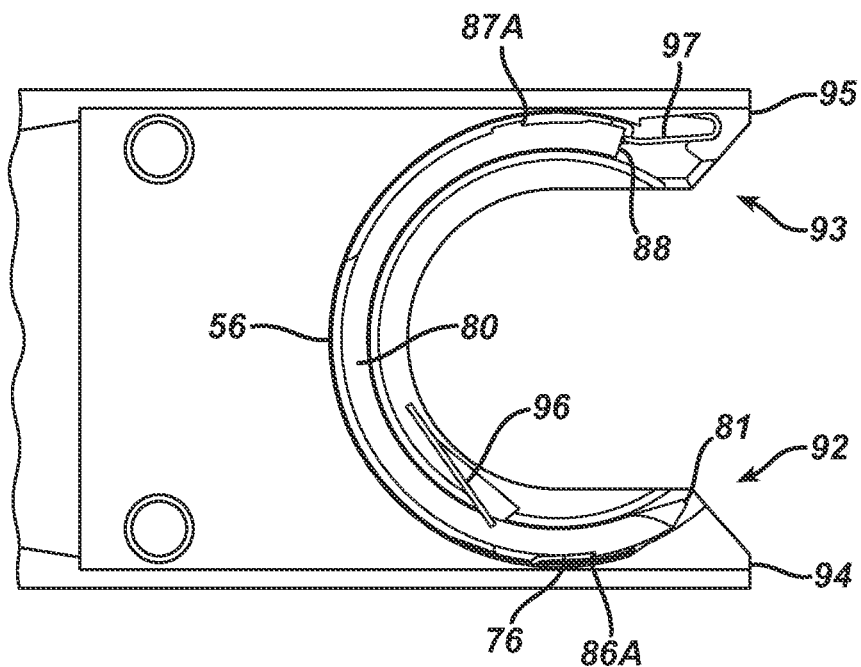
FIG. 16D depicts a plan view of a needle applier with a needle in its retracted position and the needle driver in its driven position.
Figure 17:
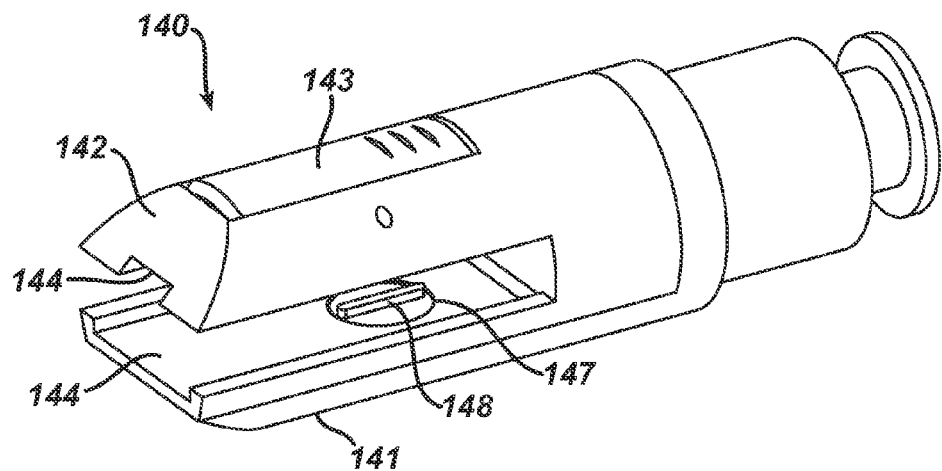
FIG. 17 depicts a perspective view of a cartridge receiver.
Figure 18:
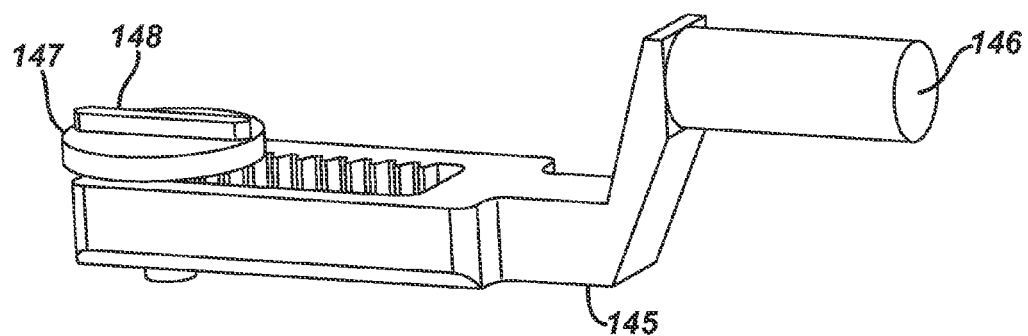
FIG. 18 depicts a perspective view of a rotary drive.
Figure 19:
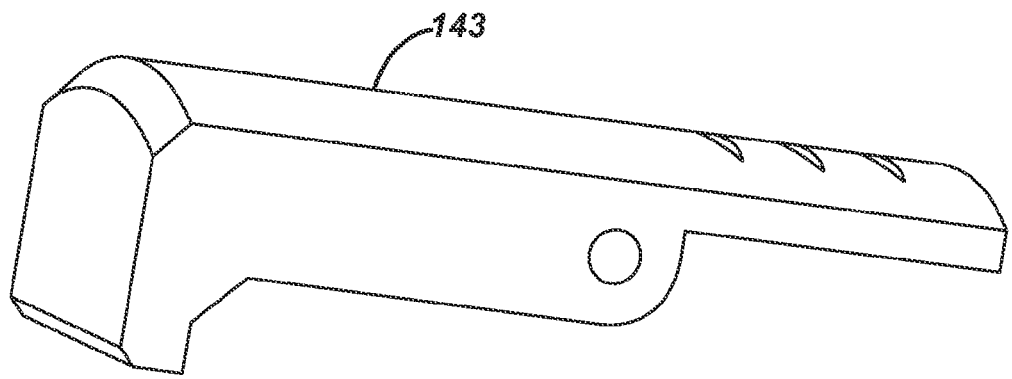
FIG. 19 depicts a perspective view of a latch.
Figure 20:
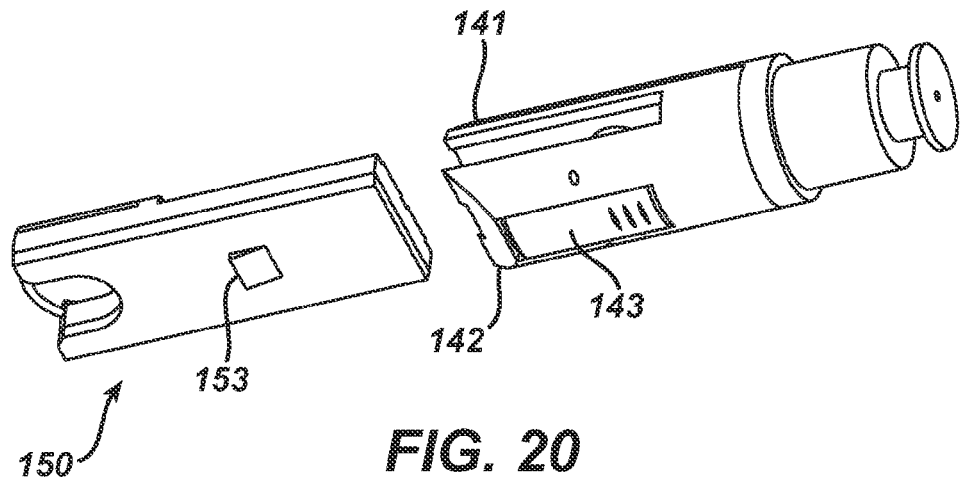
FIG. 20 depicts a perspective view of a cartridge disassembled from a receiver.
Figure 21:
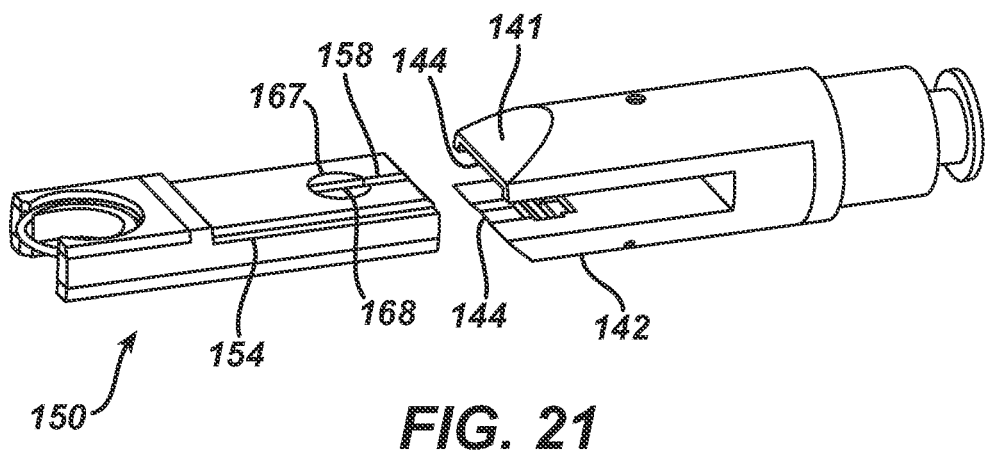
FIG. 21 depicts a perspective view of a cartridge disassembled from a receiver.

When the first input (12) is depressed again closing the trigger, the needle driver (70) will again be actuated through its drive stroke where it is rotated about 180 degrees counterclockwise to the driven position as shown in FIG. 16D. During the drive stroke, the driver (76) engages the distal step (86A) and will in unison rotate the needle (80) about 180 degrees back to its retracted position. The suture will follow the needle (80) and be threaded through the pieced tissue.

When the first input (12) is again released and the spring return opens the trigger, the needle driver (70) again reciprocates through its return stroke where it is rotated about 180 degrees clockwise back to its returned position as shown in FIG. 16A. During the return stroke the driver (76) slides over the needle (80) and the leaf spring (97) engages the trailing face (88) preventing the needle (80) from rotating clockwise. Thus, the needle (80) is driven in a complete circular path. The sequence may be repeated as needed by the surgeon to achieve the desired suturing task.

FIGS. 17-21 illustrate another embodiment of a receiver (140) located on the distal end (22) of the shaft (20). The receiver has an axially off-set lower arm (141) and an axially off-set upper arm (142), each having a longitudinal slot (144). A spring loaded latch (143) is adapted to selectively lock and unlock the cartridge (150) in the receiver (140). A rack (145) and pinion (147) rotary drive is positioned in the lower arm (141). The inner cable of the co-axial torsion tube (28) is connected to the proximal end (146) of the rack (145). The rack (145) is bent to accommodate the axial off-set of the lower arm (141). The key (148) mates with the slot (168) to translate the reciprocating rotation of the pinion (147) to the rotary input (168) in the cartridge (150).

The disposable cartridge (150) is adapted to be attached to the receiver (140). The cartridge (150) may be slid proximally between the arms (141, 142) of the receiver (140) until the latch (143) engages the step (152). The step (154) mates with the longitudinal slot (144) in the lower arm (141), and the step (152) mates with the longitudinal slot (144) in the upper arm (142). The slot (158) is dimensioned to receive the key (148) while the cartridge (150) is being slid onto the receiver (140). When the cartridge (50) is fully seated into the receiver (140), the pinion (147) is axially aligned with rotary input (167) and the key (148) is positioned in the slot (168) thereby rotationally coupling the rotary drive to the rotary input (167).

Figure 22A:
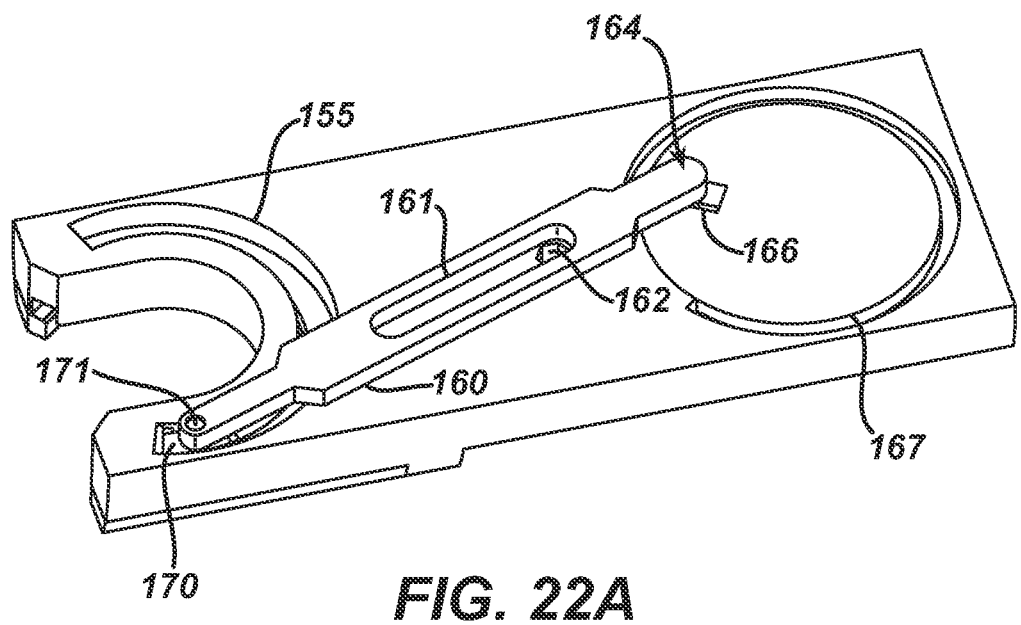
FIG. 22A depicts a perspective view of a transmission for driving a needle at one end of its stroke.
Figure 22B:
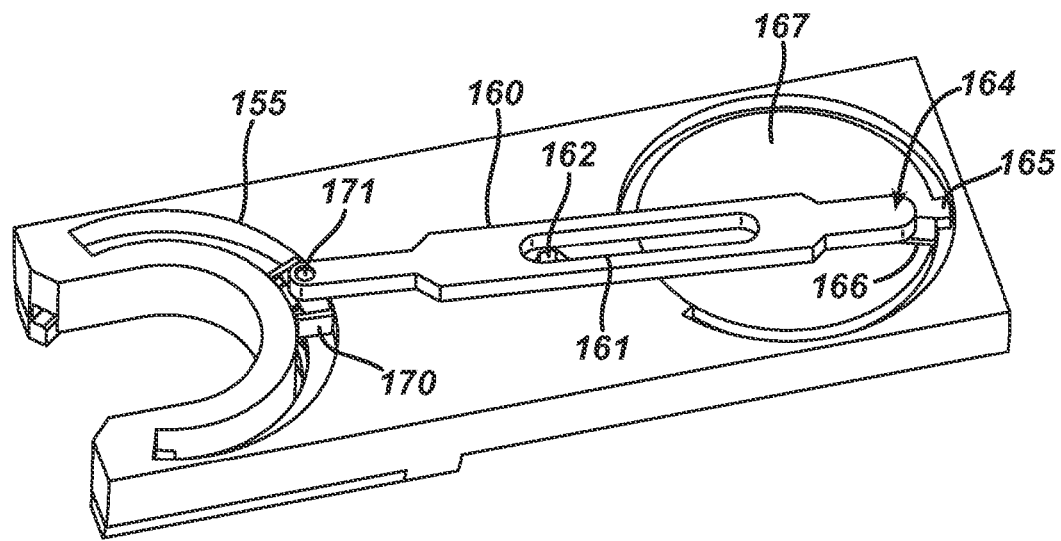
FIG. 22B depicts a perspective view of a transmission for driving a needle at mid-stroke.
Figure 22C:
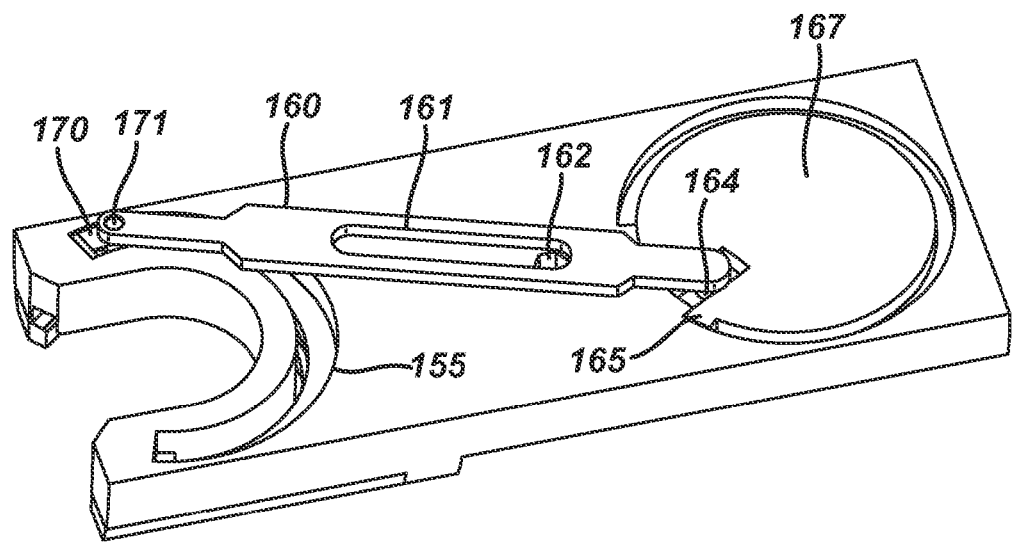
FIG. 22C depicts a perspective view of a transmission for driving a needle at the other end of its stroke.

FIGS. 22A-C illustrate one example of a transmission in the cartridge (150) for driving a needle in a circular path. A needle driver (170) reciprocates in the arced carrier track (155). A straight link (160) connects the rotary input (167) to the needle driver (170). The pin (171) pivotally connects the distal end of the link (160) to the needle driver (170). The rotary input (167) a radial slot (166). The pin (164), hidden from view below the link (160), is positioned in the slot (166) to connect the proximal end of the link (160) to the rotary input (167). The slot (166) rotationally constrains the pin (164) while accommodating some relative radial movement. The link (160) has a longitudinal slot (161) receiving the fixed pin (162) about which the link (160) both longitudinally translates and pivots. The needle driver (170) and rotary input (167) are co-planar. A tooth (165) engages stops in the cartridge to limit the rotational stoke of the rotary input (167).

FIG. 22A illustrates the needle driver (170) positioned at one end of it stroke in the carrier track (155). As shown in FIG. 22B, clockwise rotation of the rotary input (167) will translate the needle driver (170) counterclockwise along the carrier track (155). As shown in FIG. 22C, continued clockwise rotation of the rotary input (167) will continue translate the needle driver (170) counterclockwise until it reaches the other end of its stroke in the carrier track (155). The rotary input (167), link (160), and needle driver (170) have no indeterminate point, so rotation of the rotary input (167) will cause the needle driver (170) to translate in the opposite rotational direction throughout the stroke without binding. The sequence can be reversed by rotating the rotary input (167) counterclockwise, which will translate the needle driver (170) clockwise in the carrier track (55).

Figure 23A:
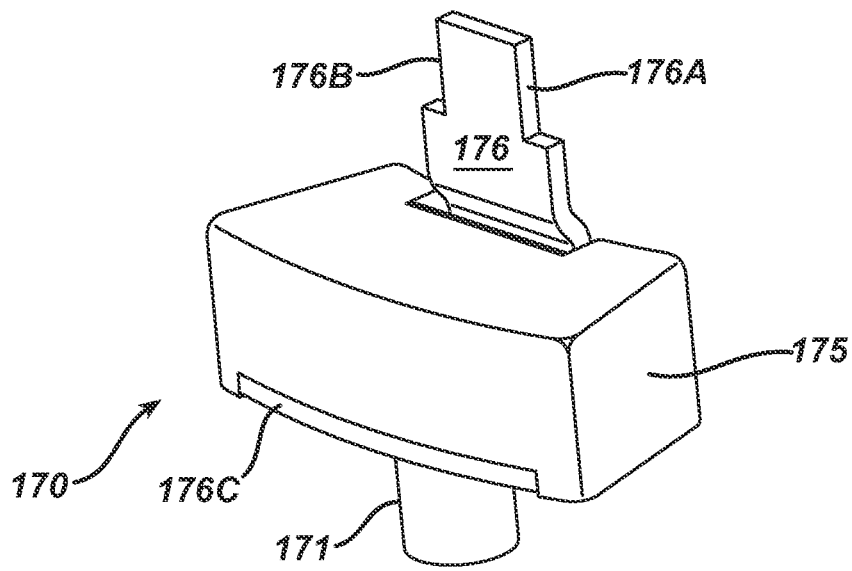
FIG. 23A depicts a perspective view of a needle driver.
Figure 23B:
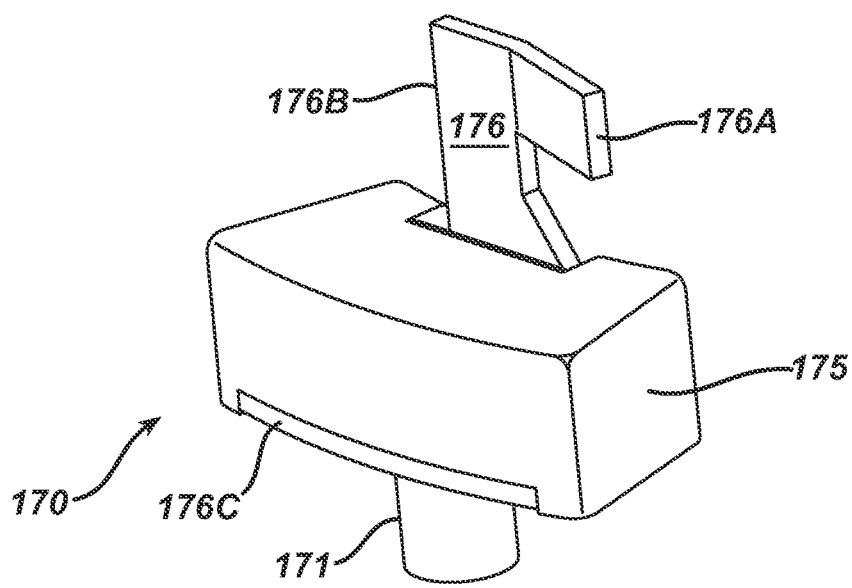
FIG. 23B depicts a perspective view of a needle driver.

FIG. 23A illustrates one embodiment of a needle driver (170). A carrier (175) is dimensioned to slideably fit in the carrier track (155). The carrier (175) may be a monolithic component with an arced shaped. The pin (171) extends from the carrier (175). The driver (176) extends from the carrier (175) through the slot (157) and into the needle track (156). The driver (176) is an L-shaped metal blade with one leg (176C) having a hole that fits over the pin (171) and is seated against the carrier (175). The driver (176) has a drive face (176A) and a return face (176B). In this embodiment, the drive face (176A) and return face (176B) are generally co-planar and symmetrical. FIG. 23B shows another embodiment where the drive face (176A) is bent toward the needle (180).

Figure 24:
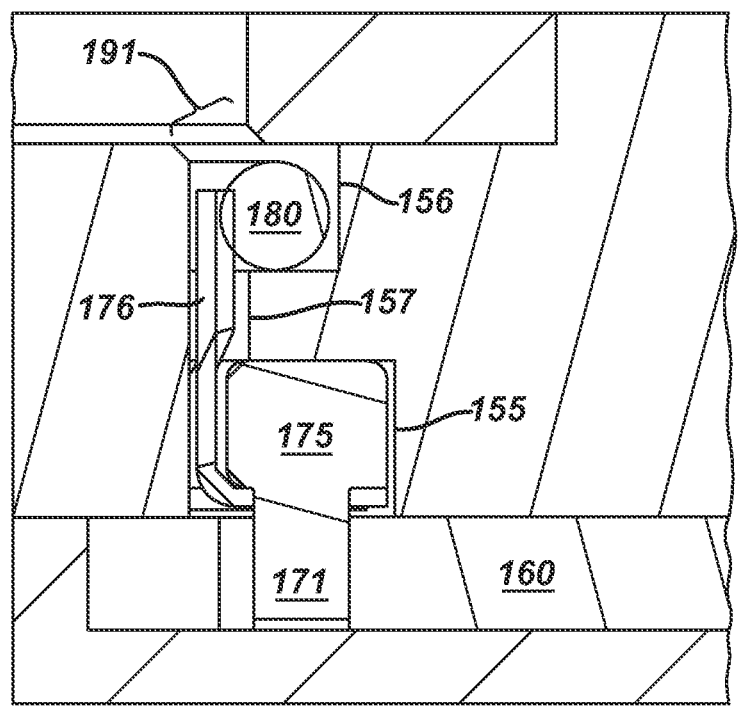
FIG. 24 depicts a cross-sectional view of a needle driver in a carrier track and a needle in a needle track.

As shown in FIG. 24, the needle track (156) and carrier track (155) are co-axial and co-radial. The tracks (155, 156) are off-set along the shared axis from one another with a wall separating the tracks (155, 156). A slot (157) opens through the wall and provides communication between the carrier track (155) and the needle track (156). In this embodiment the slot (157) opens adjacent the medial edge of the needle track (156). The needle (180) slideably fits in the needle track (156) and the carrier (175) slideably fits in the carrier track (155). The driver (176) extends through the slot (157) and into the needle track (156). The driver (176) is arranged as a cantilever leaf spring resiliently engaging the medial face of the needle (180). As the needle (180) is rotated in the needle track (156), the suture may extend out through the window (191).

Figure 25A:
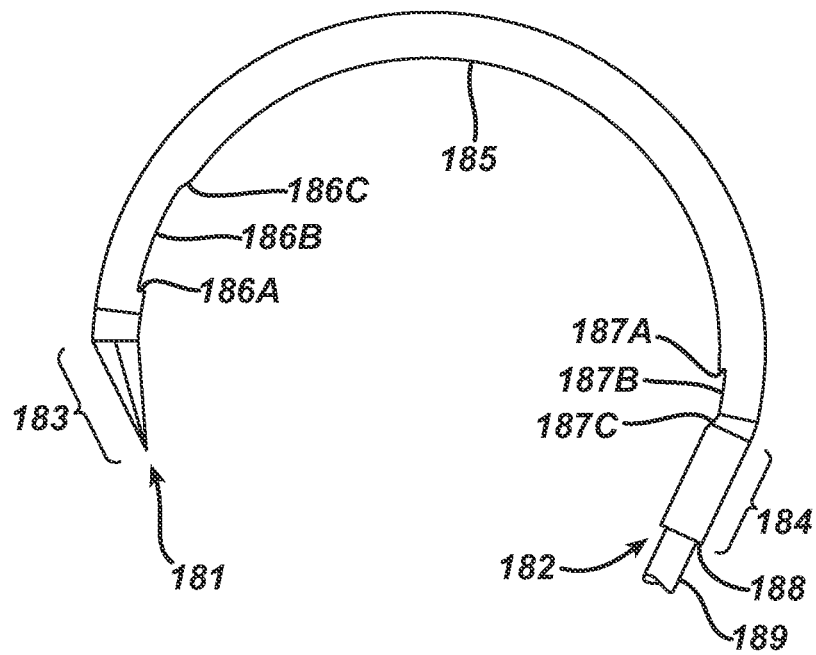
FIG. 25A depicts a plan view of arced needle.
Figure 25B:
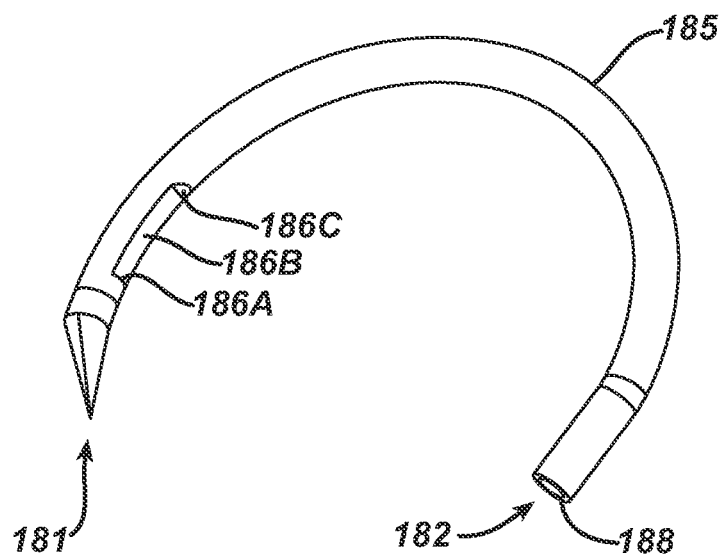
FIG. 25B depicts a perspective view of arced needle.

FIGS. 25A-B illustrates an embodiment of a needle (180) having a distal leading end (181) with a sharp tapered tip (183). The proximal trailing end (182) has a tubular barrel (184) that fixedly receives a length of suture (189). A trailing face (188) circumscribes the suture (189). An arced body (185) extends between the tapered tip (183) and barrel (184). A distal step (186A) is positioned on the medial face of the body (185). The distal step (186A) may be located between about 20 degrees and about 30 degrees from the leading end (181). A proximal step (187A) is positioned on the medial face of the body (185) about 180 degrees from the distal step (186A). The steps (186A, 187A) are adapted to be engaged by the driver (176) of the needle driver (170). Flats (186B, 187B) extend distally from the steps (186A, 187A) and define a generally D-shaped cross sectional shape in the body (185). The distal flat (186B) has an angular span between about 20 degrees and about 40 degrees from the distal step (186A). The proximal flat (187B) has an angular span between about 8 degrees and about 20 degrees from the distal step (187A). Ramps (186C, 187C) are located adjacent the proximal ends the flats (186B, 187B) such that the cross-sectional shape of the body (185) transitions from a generally D-shape to a generally circular shape. The steps (186A, 187A), flats (186B, 187B), and ramps (186C, 187C) may be made by plastically deforming the body (185). In addition to the advantages discussed above, the process of plastically forming the distal step (186A) may partially bend the tapered tip (183) medially, which facilitates locating the leading end (181) along the desired radius of curvature when the straight stock is bent to its arced shape.

Figure 26A:
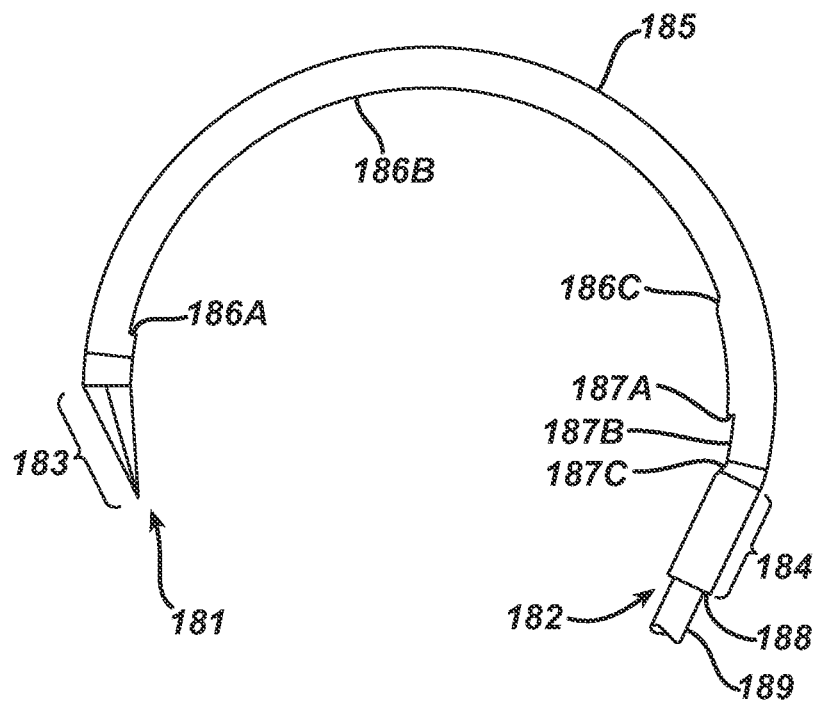
FIG. 26A depicts a plan view of arced needle.
Figure 26B:
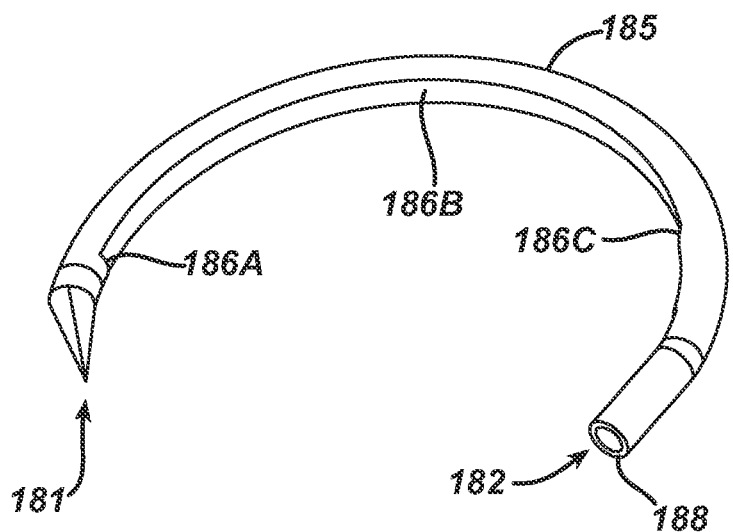
FIG. 26B depicts a perspective view of arced needle.

FIGS. 26A-B illustrates another embodiment of needle (180) substantially the same as in FIGS. 25A-B; however, the distal flat (186B) has an angular span between about 120 degrees and about 150 degrees from the distal step (186A).

FIGS. 27A-D illustrate one embodiment of a circular needle applier (30) rotating an arced needle (180) in a circular path. The suture has been hidden in the figures to better illustrate device operation. A pair of arms (194, 195) define a generally U-shaped distal end on the circular needle applier (30). The needle track (156) has an exit port (192) in arm (194) and an entrance port (193) in arm (195). The leaf springs (196, 197) allow the needle (180) to rotate counterclockwise, but prevent the needle (180) from rotating clockwise. Leaf spring (197) extends into the needle track (156) and resiliently deflects laterally when engaging the lateral face of the needle (180). Leaf spring (196) extends into the needle track (156) and resiliently deflects laterally when engaging the lateral face of the needle (180). The leaf springs (196, 197) are spaced about 180 degrees from one another.

Figure 27A:
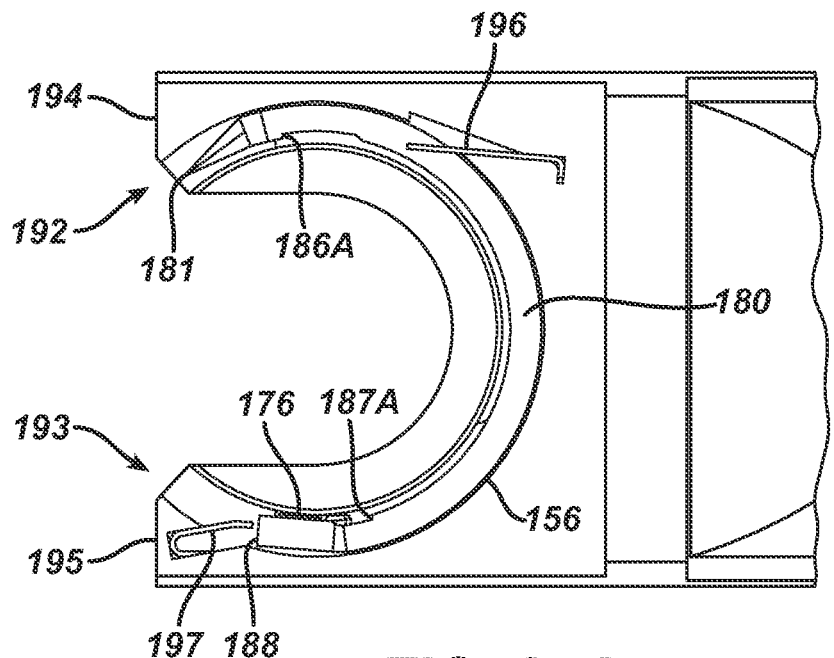
FIG. 27A depicts a plan view of a needle applier with a needle in its retracted position and the needle driver in its returned position.

FIG. 27A shows the device in its initial position. The needle (180) is in its retracted position and completely contained in the needle track (156). The needle driver (170) is in its returned position in arm (195). The driver (176) is adjacent the proximal step (187A). Leaf spring (197) is adjacent the trailing face (188) preventing the needle (180) from rotating clockwise.

Figure 27B:
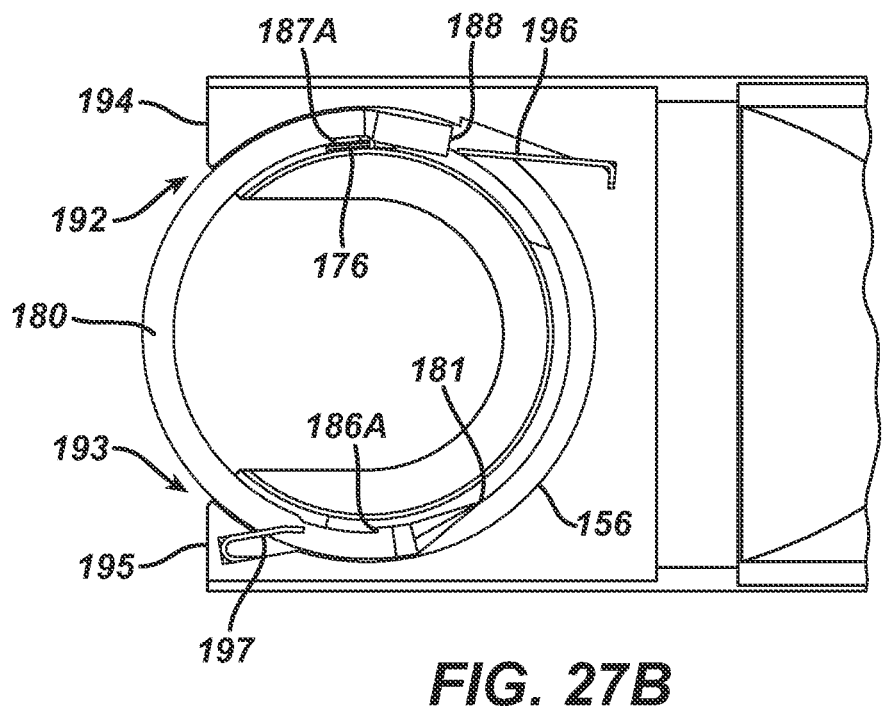
FIG. 27B depicts a plan view of a needle applier with a needle in its extended position and the needle driver in its driven position.

When the needle driver (170) is actuated through its drive stroke, it is rotated about 180 degrees counterclockwise to the driven position as shown in FIG. 27B. During the drive stroke, the driver (176) engages the proximal step (187A) and will in unison rotate the needle (180) about 180 degrees to its extended position. The needle (180) will span across the arms (194, 195) between the exit port (192) and the entrance port (193). Tissue interposed between the arms (194, 195) will be pieced by the leading end (181) of the needle (180).

Figure 27C:
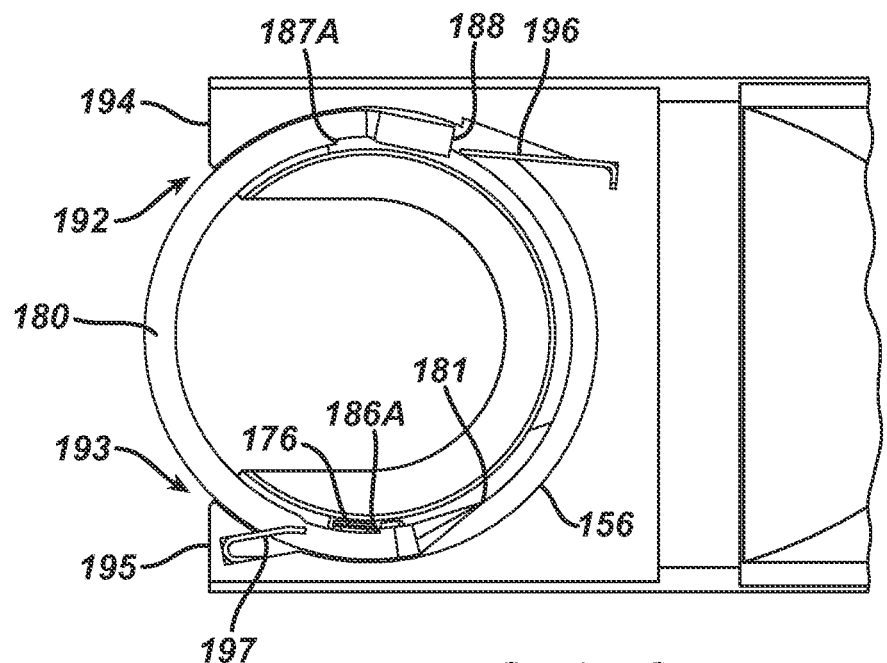
FIG. 27C depicts a plan view of a needle applier with a needle in its extended position and the needle driver in its returned position.

When the needle driver (170) reciprocates through its return stroke, it is rotated about 180 degrees clockwise back to the return position shown in FIG. 27C. During the return stroke the driver (176) slides over the needle (180) and the leaf spring (196) engages the trailing face (188) preventing the needle (180) from rotating clockwise.

Figure 27D:
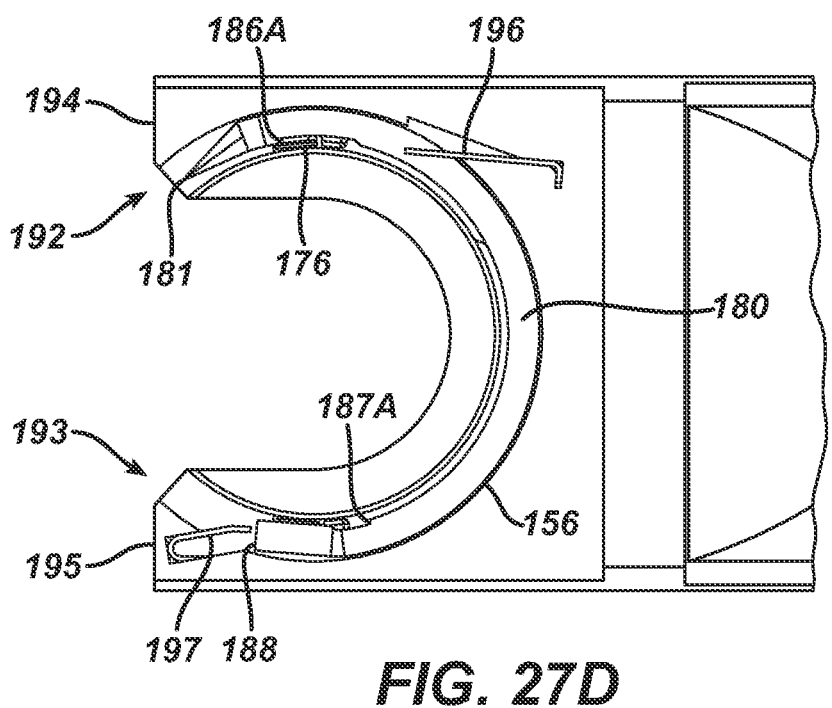
FIG. 27D depicts a plan view of a needle applier with a needle in its retracted position and the needle driver in its driven position.

When the needle driver (170) is actuated through its drive stroke, it is rotated about 180 degrees counterclockwise to the driven position as shown in FIG. 27D. During the drive stroke, the driver (176) engages the distal step (186A) and will in unison rotate the needle (180) about 180 degrees back to its retracted position. The suture will follow the needle (180) and be threaded through the pierced tissue.

When the needle driver (170) reciprocates through its return stroke, it is rotated about 180 degrees clockwise back to its returned position as shown in FIG. 27A. During the return stroke the driver (176) slides over the needle (180) and the leaf spring (197) engages the trailing face (188) preventing the needle (80) from rotating clockwise. Thus, the needle (180) is driven in a complete circular cycle.

Figure 28:
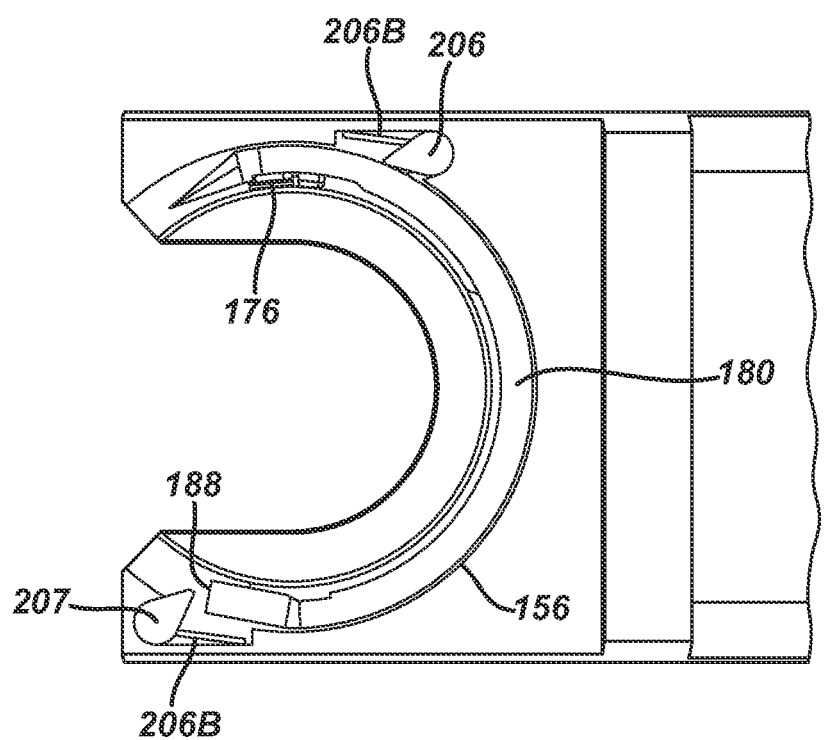
FIG. 28 depicts a plan view of a needle applier with a needle in its retracted position and the needle driver in its driven position.

FIG. 28 illustrates a variation using pawls (206, 207) to allow the needle (180) to rotate counterclockwise, but prevent the needle (180) from rotating clockwise. Each pawl (206, 207) is generally "tear-drop" shaped having a rounded end and a pointed end with an edge. The pawls (206, 207) pivot around the rounded end in the same plane as the needle (180) such that the pointed end can rotate in and out of the needle track (156). Spring (206B, 207B) bias the pointed ends medially into the needle track (156). The pointed ends extend into the needle track (156) and resiliently deflect laterally when engaging the lateral face of the needle (180), thus allowing counterclockwise motion. But when the needle (180) passes one of the pawls (206, 207), the pointed ends will deflect medially into the path to interfere and engage the trailing face (188), thus preventing the needle (180) from rotating clockwise.

FIGS. 29A-D illustrate another embodiment of a circular needle applier (30). Pawls (216, 217) allow the needle (180) to rotate counterclockwise in the needle track (156), but prevent the needle (180) from rotating clockwise. In this embodiment, pawls (216, 217) engage and act on the same features of the needle (180) as the needle driver (170). While illustrated with two pawls (216, 217), it will be appreciated that their function is redundant and the device can operate with only one of the pawls (216, 217) present.

Pawl (216) is generally aligned with the driven position of the driver (176). Pawl (216) translates transverse to the needle (180) path and in the plane of the needle (180). A spring (216B) biases the pawl (216) laterally into the needle track (156). As the needle (180) rotates counterclockwise, the needle (180) or driver (176) will engage the ramp (216A) to deflect the pawl (216) medially, thus allowing counterclockwise motion. Pawl (217) is generally aligned with the returned position of the driver (176). Pawl (217) can translate radially in the plane of the needle (180). A spring (217B) biases the pawl (217) laterally into the needle track (156). As the needle (180) rotates counterclockwise, the needle (180) or driver (176) engages the ramp (217A) to deflect the pawl (217) medially, thus allowing counterclockwise motion.

Figure 29A:
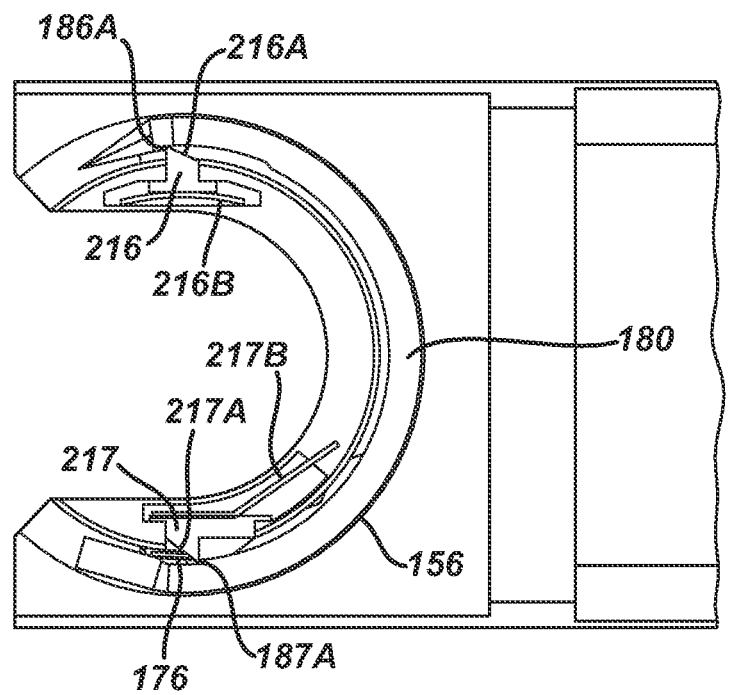
FIG. 29A depicts a plan view of a needle applier with a needle in its retracted position and the needle driver in its returned position.

FIG. 29A shows the device in its initial position. The needle (180) is in its retracted position and the needle driver (170) is in its returned position. Pawl (216) is adjacent the distal step (186A) and pawl (217) is adjacent the proximal step (187A), both preventing clockwise rotation.

Figure 29B:
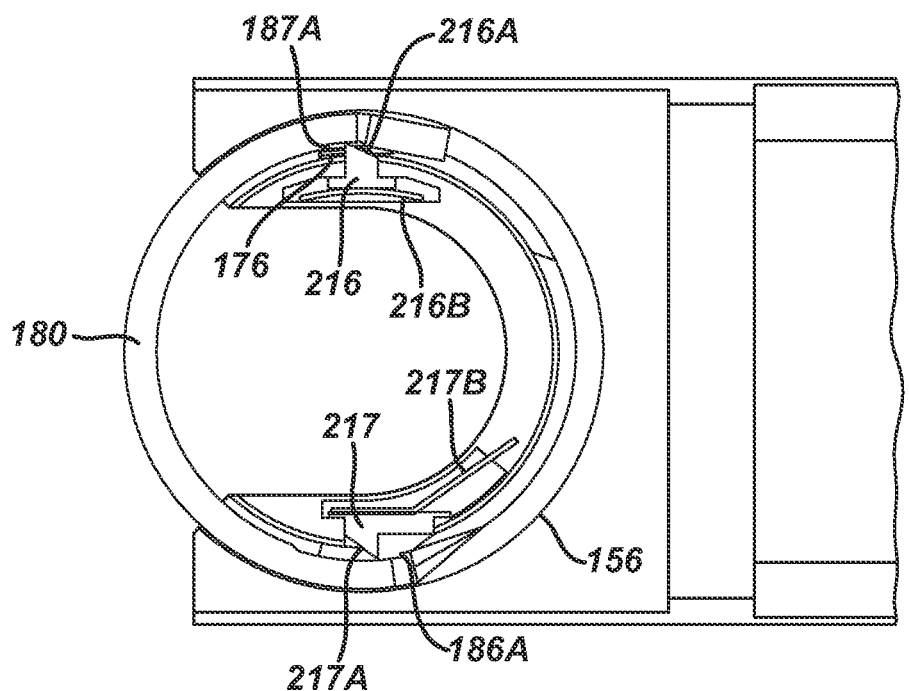
FIG. 29B depicts a plan view of a needle applier with a needle in its extended position and the needle driver in its driven position.
Figure 29C:
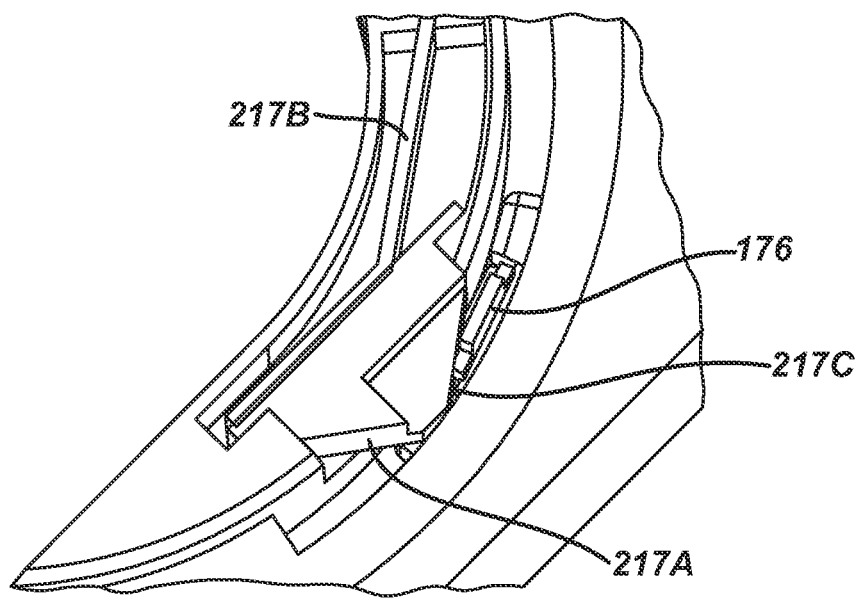
FIG. 29C depicts a perspective view of a pawl mechanism.

When the needle driver (170) is actuated through its drive stroke, it is rotated about 180 degrees counterclockwise to the driven position as shown in FIG. 29B. During the drive stroke, the driver (176) engages the proximal ramp (217A) and medially displace the pawl (217), then engages the proximal step (187A), and then in unison rotates the needle (180) about 180 degrees to its extended position. In the extended position, the pawl (217) is adjacent the distal step (186A) preventing the needle (180) from rotating clockwise. As the driver (176) approaches the driven position, the driver (176) will engage the ramp (216A) and medially displace the pawl (216). In the driven position, the driver (176) will remain interposed between the pawl (216) and the needle (180).

Figure 29D:
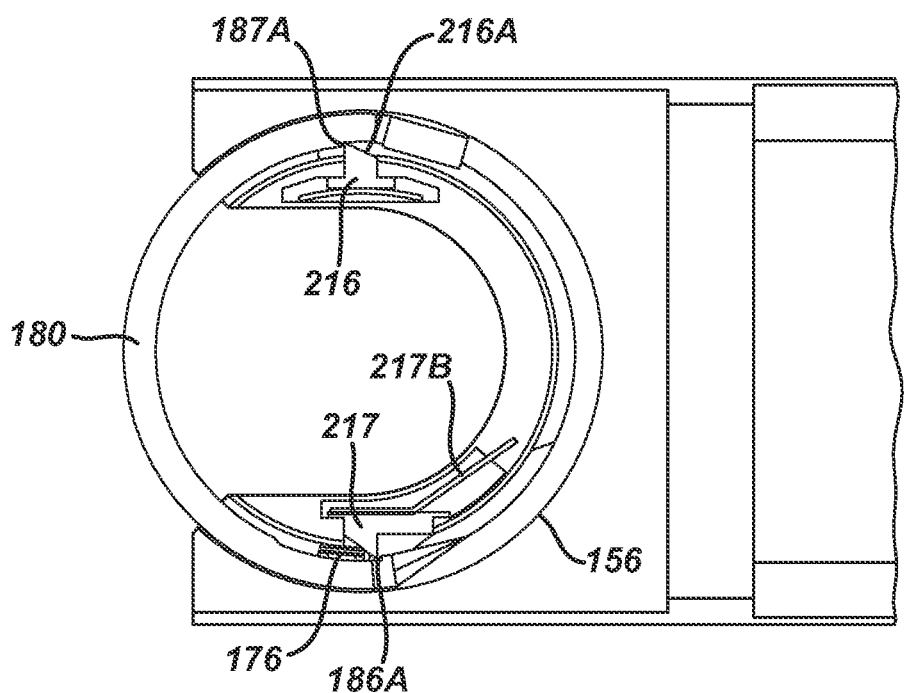
FIG. 29D depicts a plan view of a needle applier with a needle in its extended position and the needle driver in its returned position.

When the needle driver (170) reciprocates through its return stroke, it is rotated about 180 degrees clockwise back to the return position shown in FIG. 29D. As the driver (176) passes, the pawl (216) deflects adjacent the proximal step (187A) preventing the needle (180) from rotating clockwise. As illustrated in the FIG. 29C, the pawl (217) has a distal ramp (217C) positioned below needle steps (186A, 187A). For instance, the distal ramp (217C) may be positioned in the slot (157) while the proximal ramp (217A) is positioned in the needle track (156). During the return stroke, the driver (176) engages the proximal ramp (216C) and medially displaces the pawl (216). As the driver (176) passes, the pawl (217) deflects adjacent the distal step (186A) preventing the needle (180) from rotating clockwise.

The sequence can then be repeated to drive the needle (180) about 180 degrees to is retracted position.

Figure 30A:
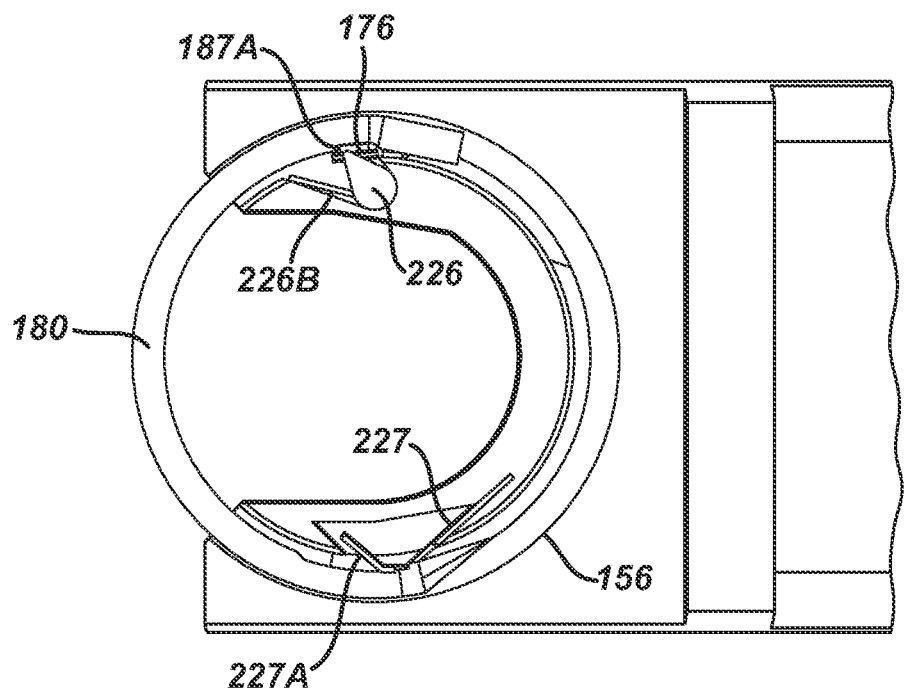
FIG. 30A depicts a plan view of a needle applier with a needle in its extended position and the needle driver in its driven position.
Figure 30B:
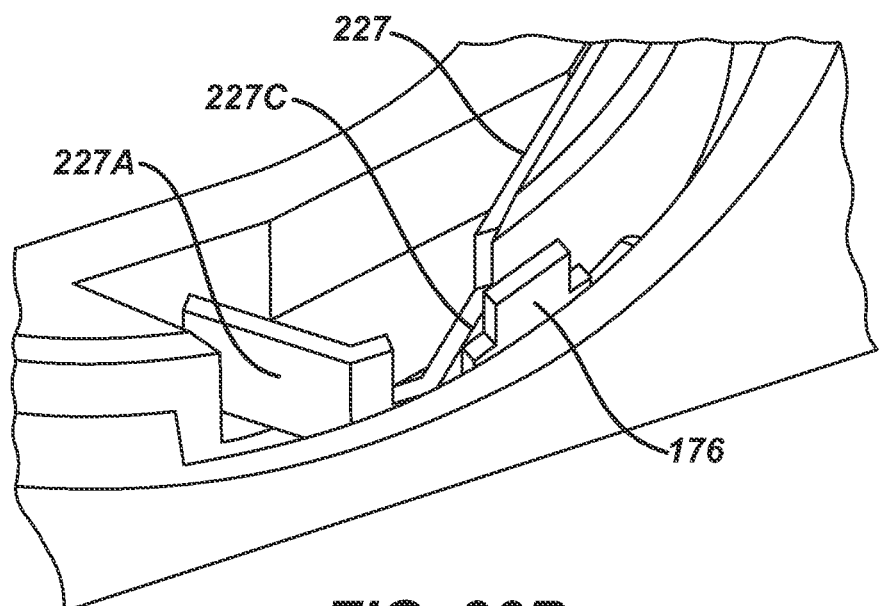
FIG. 30B depicts a perspective view of a pawl mechanism.

FIGS. 30A-B illustrate a variation of pawls (226, 227) that engage and act on the same features of the needle (180) as the needle driver (170). While illustrated with two pawls (226, 227), it will be appreciated that their function is redundant and the device can operate with only one of the pawls (226, 227) present.

Pawl (226) is generally aligned with the driven position of the driver (176). Pawl (226) is generally "tear-drop" shaped and functions similar to the pawls (206, 207). A torsional spring (226B) biases the pointed end laterally into the needle track (156). As the driver (176) approaches the driven position, the driver (176) will engage and medially displace the pointed end of the pawl (226). In the driven position, the driver (176) will remain interposed between the pawl (226) and the needle (180). When the needle driver (170) reciprocates through its return stroke, the driver (176) passes and the pawl (226) deflects adjacent the proximal step (187A) preventing the needle (180) from rotating clockwise. Pawl (226) may be substituted for a leaf spring similar in construction as leaf springs (96, 97) that would engage and act on the same features of the needle (180) as the needle driver (170).

Pawl (227) is biased laterally into the needle track (156) and functions similar to the pawl (217) in its sequence of engagement between the driver (176) and needle (180). The proximal ramp (227A) is positioned in the needle track (156) and allows the needle (180) and driver (176) to pass as they rotate counterclockwise. The distal ramp (227C) is positioned in the slot (157) so that during the return stroke, the driver (176) engages the proximal ramp (216C) and medially displaces the pawl (216).

Figure 31A:
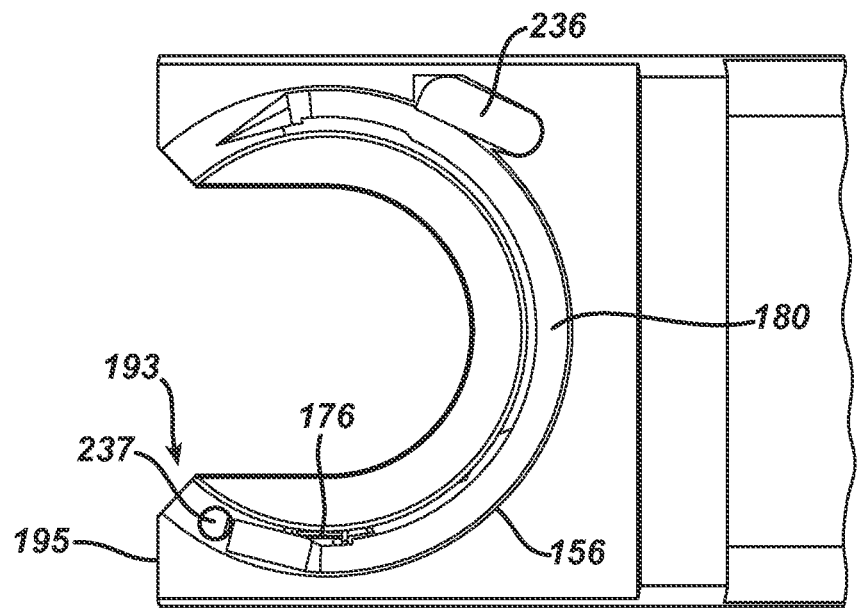
FIG. 31A depicts a plan view of a needle applier with a needle in its retracted position and the needle driver in its returned position.
Figure 31B:
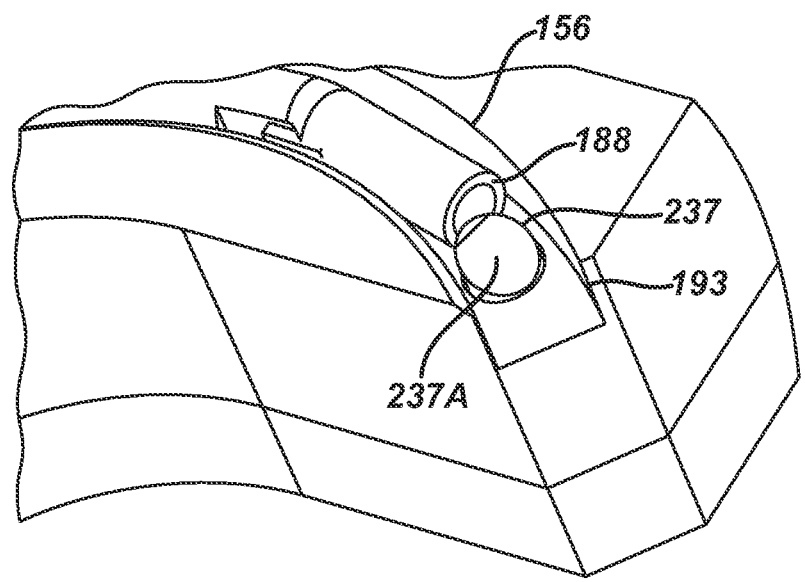
FIG. 31B depicts a perspective view of a pawl mechanism.
Figure 31C:
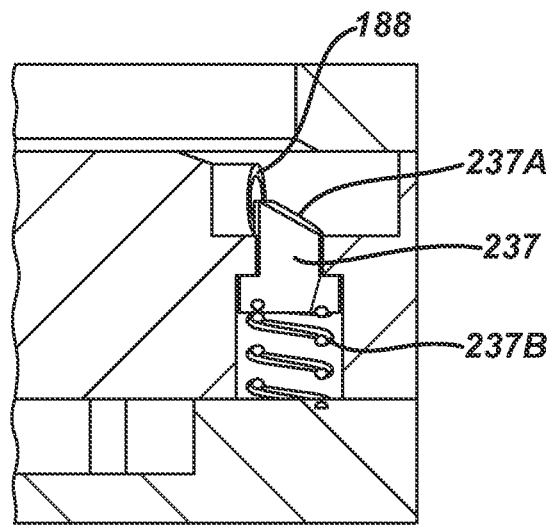
FIG. 31C depicts a cross-sectional view of a pawl mechanism.

FIGS. 31A-C illustrate another embodiment of pawls (236, 237) that allow the needle (180) to rotate counterclockwise, but prevent the needle (180) from rotating clockwise. Pawl (236) is generally oval shaped with one end partially angled to an edge. The pawl (236) pivots around the rounded end in the same plane as the needle (180) such that the edge can rotate in and out of the needle track (156). A torsional spring biases the edge medially into the needle track (156). The pawl (236) functions similar to the pawl (206) in its sequence of engagement needle (180) and the trailing face (188).

Pawl (237) is located in the arm (195) adjacent the entrance port (193). The pawl (237) is positioned below the needle track (156) and translates at an angle transverse, and optionally perpendicular, to the plane of the needle (180). A spring (237B) biases the pawl (237) upward into the needle track (156). As the needle (180) rotates counterclockwise, the needle (180) engages the ramp (237A) to deflect the pawl (237) downward, thus allowing counterclockwise motion. But when the needle (180) passes the pawl (237), it will deflect into the path to interfere and engage the trailing face (188), thus preventing the needle (180) from rotating clockwise.

Figure 32:
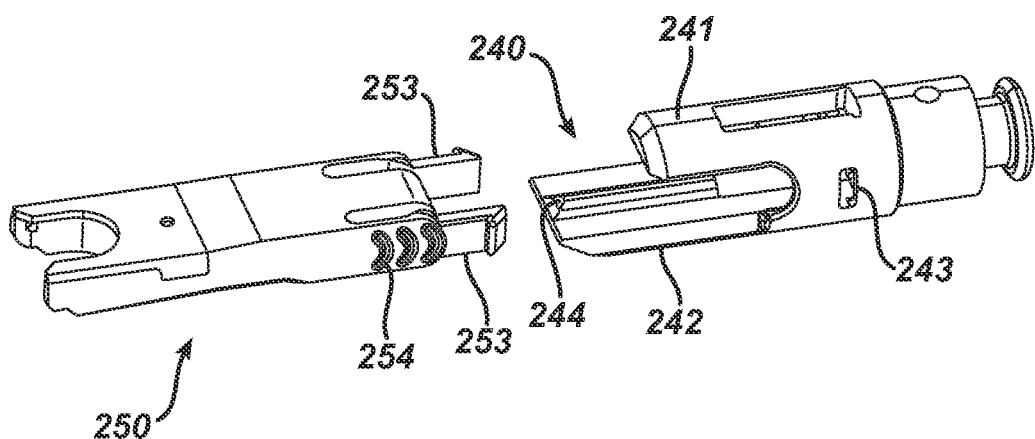
FIG. 32 depicts a perspective view of a cartridge disassembled from a receiver.

FIG. 32 illustrates another embodiment of a cartridge (250) and receiver (240). The cartridge (250) may be similar to any of the prior described cartridges, and contains a surgical needle, a length of suture connected to the surgical needle, a needle driver operative to engage and move the needle relative the cartridge, and a transmission operatively connected to the needle driver. The receiver (240) has an axially off-set lower arm (141) and an axially off-set upper arm (142). The lower arm (242) extends more distally than the upper arm (241). The lower arm (242) has a longitudinal ridge (244) that mates with a corresponding groove (not shown) on the cartridge (250). A rotary drive mechanism is located in the lower arm (242). A pair of barbed prongs (253) extend from the cartridge (250). The cartridge (250) is attached to the receiver (240) by longitudinally sliding the cartridge (250) between the arms (241, 242) until the prongs (253) seat in the holes (243), thus locking the cartridge (250) in the receiver (240). The cartridge (250) can be unlocked and removed by squeezing the grips (254), which will medially deflect the prongs (253) until they disengage from the holes (243), at which point the cartridge (250) can be pulled from the receiver (240).

Figure 33:
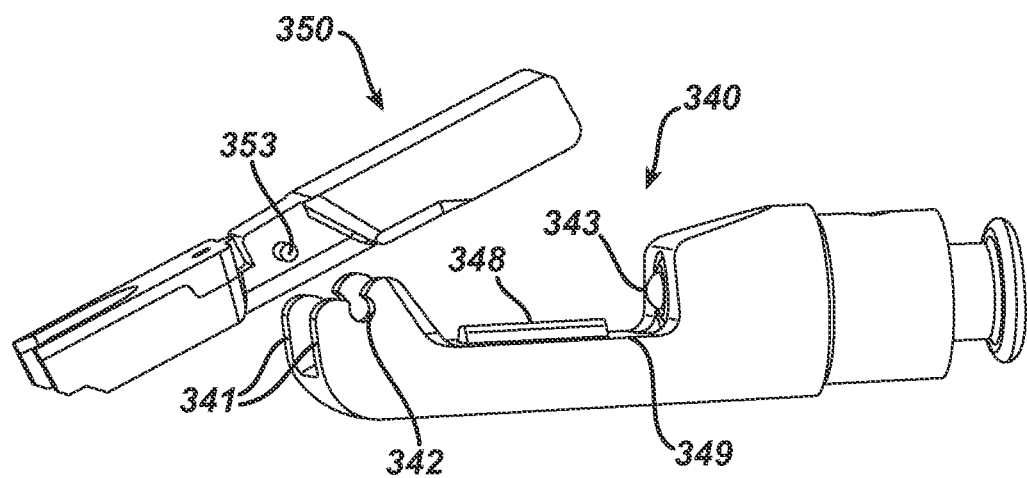
FIG. 33 depicts a perspective view of a cartridge disassembled from a receiver.

FIG. 33 illustrates another embodiment of a cartridge (350) and receiver (340). The cartridge (350) may be similar to any of the prior described cartridges, and contains a surgical needle, a length of suture connected to the surgical needle, a needle driver operative to engage and move the needle relative the cartridge, and a transmission operatively connected to the needle driver. The receiver (340) has a longitudinal deck through which a key (348) translates the reciprocating rotation of a rotary drive to the transmission in the cartridge (350). A pair of spaced apart flanges (341) are adjacent the distal end of the deck (349). Each flange (341) has a pin hole (342). The cartridge (350) is attached to the receiver (340) by snapping the pins (353) into the pin holes (342). The cartridge (350) is then rotated about the pins (353) until it engages the deck (349). A detent mechanism (343) engages a matching recess in the cartridge (350) to lock the cartridge (350) in the receiver (340). The cartridge (350) can be unlocked and removed by reversing the sequence.

Figure 34:
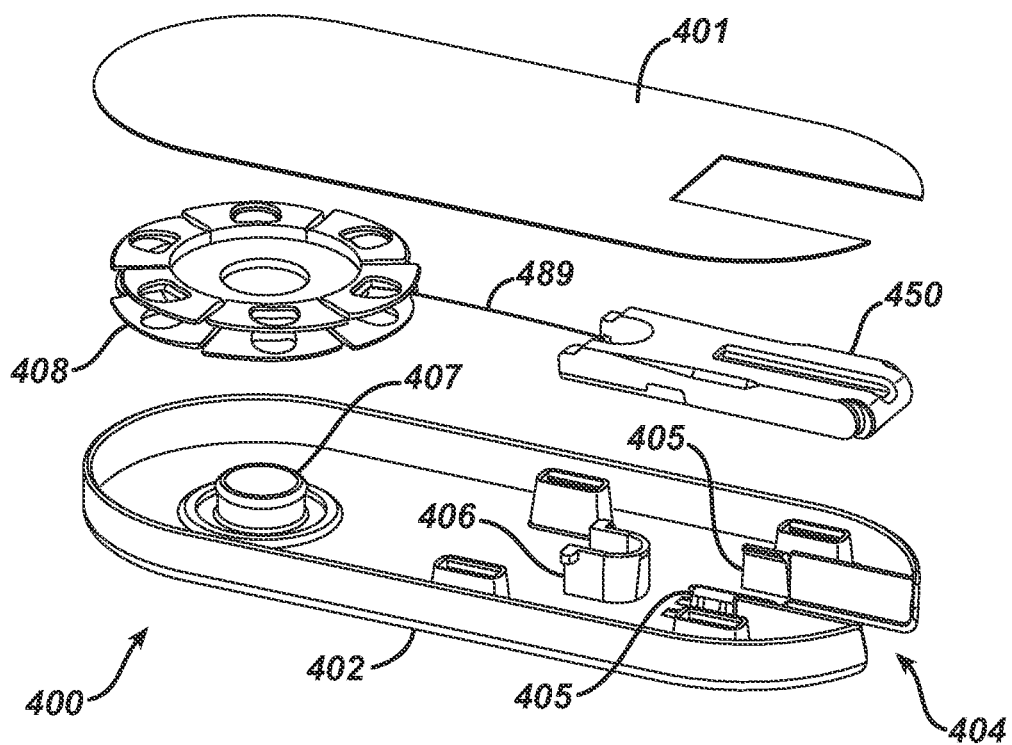
FIG. 34 depicts an exploded view of a cartridge packaging.

FIG. 34 illustrates an embodiment of packaging (400) for a cartridge (450). The cartridge (450) may be similar to any of the prior described cartridges, and contains a surgical needle, a length of suture (489) connected to the surgical needle, a needle driver operative to engage and move the needle relative the cartridge, and a transmission operatively connected to the needle driver. The packaging (400) has an outer shell comprising a housing (402) and a top sheet (401). The needle in the cartridge (450) is in its refracted position. The cartridge (450) is releasably held by arms (405). The block (406) is positioned in the U-shaped distal end on the cartridge (450) and prevents the needle from exiting the cartridge (450). The cartridge (450) extends into the gap (404). The suture (489) extends from the cartridge (450) and is coiled around the bobbin (408), shown here as a dynamic spool that can rotate about the axle (407). The bobbin (408) can take alternatively take the form of a static bobbin, such as pegs or a track, around which the suture (489) can be coiled.

Figure 35:
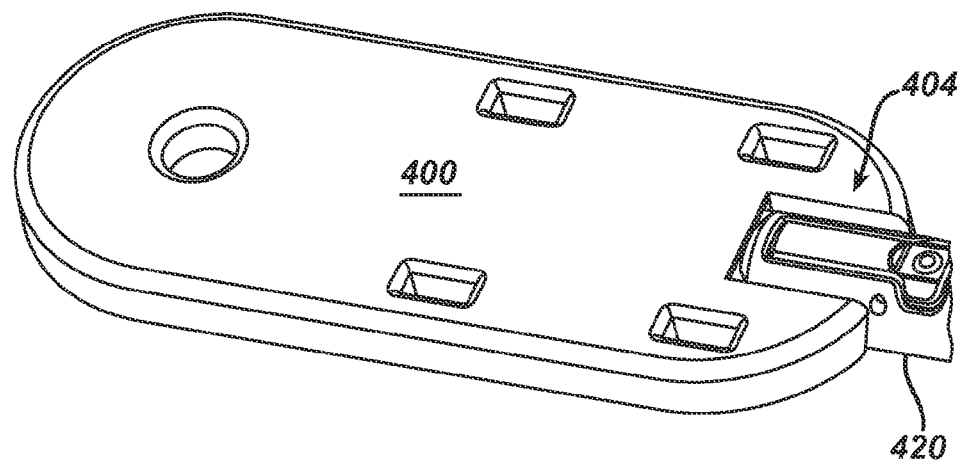
FIG. 35 depicts a perspective view of a cartridge being attached to a suturing device shaft.

As shown in FIG. 35, the packaging (400) facilitates assembly of the cartridge (400) onto a suturing device (420). The packaging (400) provides an ergonomically friendly format to handle, align, and assembly the cartridge (400) onto the shaft (420) of a suturing device, while keeping the needle safely isolated from the user. Once assembled and attached, withdrawing the shaft (420) will pull the cartridge (400) from packaging (400) and the suture (489) will reel out from the bobbin (408) and be ready for use.

Figure 36:
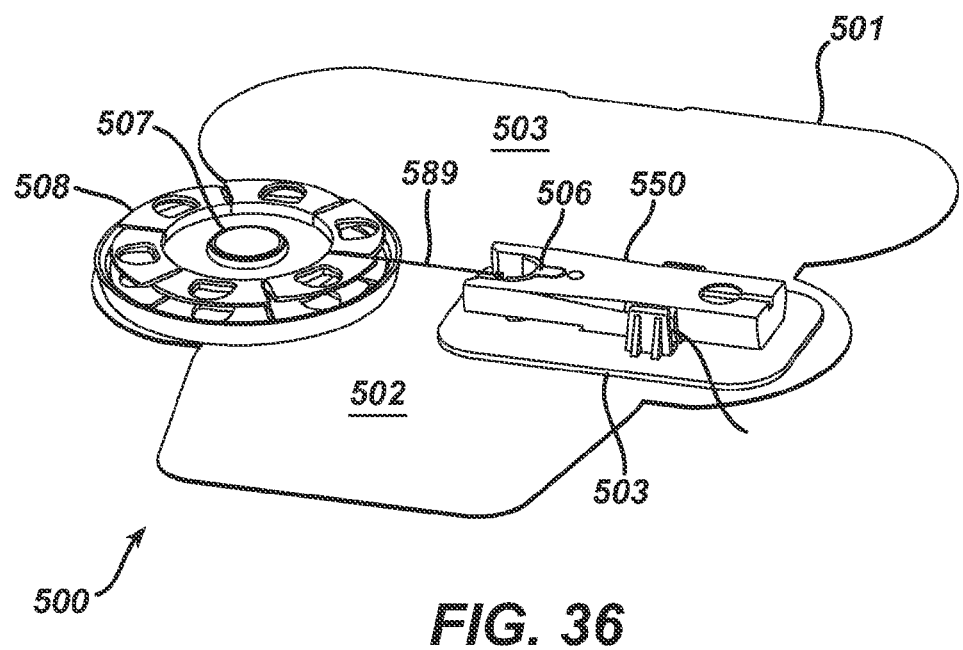
FIG. 36 depicts a perspective view of a cartridge packaging.

FIG. 36 illustrates another embodiment of packaging (500) for a cartridge (550). The cartridge (550) may be similar to any of the prior described cartridges, and contains a surgical needle, a length of suture (589) connected to the surgical needle, a needle driver operative to engage and move the needle relative the cartridge, and a transmission operatively connected to the needle driver. The cartridge (550) is releasably held on the platform (503) between the arms (505) with the block (506) inserted into the U-shaped distal end on the cartridge (550). The suture (589) extends from the cartridge (550) and is coiled around the bobbin (508). The packaging (500) has an outer shell (501) in the form of plastic or paper sheet. The small flap (502) is folded over the bobbin (508) and cartridge (550), large flap (503) is folded over the small flap (502), thus enclosing the cartridge (550), bobbin (508), and suture (589).

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. Accordingly, the scope of the present invention should be considered in terms of the following claims and is understood not to be limited to the details of structure, materials, or acts shown and described in the specification and drawings.

The invention claimed is:

1. A surgical suturing device, comprising:
    an arced needle track;
    an arced needle slideably positioned in the needle track, the needle comprising a leading end, a trailing end, a medial face, and a lateral face;
    a length of suture connected to the needle;
    an arced carrier track spaced from the needle track;
    a reciprocating carrier having a curved body matching the arc of the carrier track, the curved body being slideably positioned in the carrier track;
    a driver extending from the carrier and positioned in the needle track and operative to engage and slide the needle in the needle track; and
    a transmission comprising a link pivotally coupled to the carrier, the transmission being operative to translate the carrier at least 180 degrees along the carrier track wherein the carrier track determines an arced path for the carrier;
    the surgical suturing device further comprising a wall separating the carrier track from the needle track; and the surgical suturing device further comprising a slotted opening through the wall, the slot communicating between the carrier track and the needle track.

2. The surgical suturing device of claim 1, wherein the driver extends through the slotted opening and into the needle track.

3. The surgical suturing device of claim 2, wherein the driver comprises a flat metal blade projecting away from the curved body and through the slotted opening.

4. The surgical suturing device of claim 2, wherein the carrier comprises a flange projecting from the curved body and dimensioned to fit in the slotted opening.

5. The surgical suturing device of claim 1, wherein the slotted opening is adjacent the medial edge of the arced needle track.

6. The surgical suturing device of claim 1, wherein the slotted opening is adjacent the lateral edge of the arced needle track.

7. The surgical suturing device of claim 1, wherein the arced needle track and arced carrier track are co-axial.

8. The surgical suturing device of claim 7, wherein the needle track and carrier track are off-set along the shared axis from one another.

9. The surgical suturing device of claim 8, wherein the needle track and carrier track are co-radial.

10. The surgical suturing device of claim 1, wherein the needle further comprises steps dimensioned and adapted to be engaged by the driver.

11. The surgical suturing device of claim 10, wherein the steps are on the medial face of the needle.

12. The surgical suturing device of claim 10, wherein the steps are on the lateral face of the needle.

13. The surgical suturing device of claim 10, wherein the driver comprises a drive face and a return face.

14. The surgical suturing device of claim 1, wherein the driver comprises a flat metal blade projecting away from the carrier.

15. A surgical suturing device, comprising:
an arced needle track;
an arced needle positioned in the needle track, the needle comprising a leading end, a trailing end, a medial face, and a lateral face;
a length of suture connected to the needle;
an arced carrier track, the arced carrier track being off-set along a shared axis with the arced needle track;
a wall separating the arced needle track from the arced carrier track, the wall comprising a slotted opening communicating between the arced carrier track and the arced needle track;
a reciprocating carrier having a curved body matching the arc of the carrier track, the curved body being slideably positioned in the arced carrier track;
a driver extending from the carrier through the slotted opening and into the arced needle track, the driver being operative to engage and slide the needle along the arced needle track; and
a transmission operative to translate the carrier along the arced carrier track wherein the arced carrier track determines an arced path for the carrier.

16. The surgical device of claim 15, wherein the transmission comprises a link pivotally coupled to the carrier.

17. The surgical device of claim 16, wherein the transmission is operative to translate the carrier at least 180 degrees along the carrier track.

\* \* \* \* \*